(12) United States Patent
Rice et al.

(10) Patent No.: US 8,093,390 B2
(45) Date of Patent: Jan. 10, 2012

(54) SUBSTITUTED FUSED [1,2]IMIDAZO[4,5-C] RING COMPOUNDS AND METHODS

(75) Inventors: Michael J. Rice, Oakdale, MN (US);
Bryon A. Merrill, River Falls, WI (US);
Philip D. Heppner, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 819 days.

(21) Appl. No.: 11/884,186

(22) PCT Filed: Feb. 10, 2006

(86) PCT No.: PCT/US2006/004736
§ 371 (c)(1),
(2), (4) Date: Aug. 11, 2008

(87) PCT Pub. No.: WO2006/086633
PCT Pub. Date: Aug. 17, 2006

(65) Prior Publication Data
US 2009/0005371 A1    Jan. 1, 2009

Related U.S. Application Data

(60) Provisional application No. 60/652,281, filed on Feb. 11, 2005.

(51) Int. Cl.
*C07D 513/00*    (2006.01)
*A61K 31/44*    (2006.01)

(52) U.S. Cl. .......................................... 546/64; 514/285

(58) Field of Classification Search .................. None
See application file for complete search history.

(56) References Cited

U.S. PATENT DOCUMENTS 5,482,936 A    1/1996    Lindstrom

*Primary Examiner* — Janet Andres
*Assistant Examiner* — Heidi Reese

(57) ABSTRACT

Fused [1,2]imidazo[4,5-c] ring compounds, e.g., fused [1,2] imidazo[4,5-c]quinolines and [1,2]imidazo[4,5-c]naphthyridines, with a substituent, e.g., a substituted alkoxy substituent, at the 6, 7, 8, or 9-position, pharmaceutical compositions containing the compounds, intermediates, methods of making and methods of use of these compounds as immunomodulators, for inducing cytokine biosynthesis in animals and in the treatment of diseases including viral and neoplastic diseases are disclosed.

14 Claims, No Drawings

SUBSTITUTED FUSED [1,2]IMIDAZO[4,5-C] RING COMPOUNDS AND METHODS

CROSS-REFERENCE TO RELATED APPLICATIONS

This application is a national stage filing under 35 U.S.C. §371 of PCT International application PCT/US2006/004736 designating the United States of America, and filed Feb. 10, 2006. This application claims the benefit under 35 U.S.C. §119 of U.S. provisional application Ser. No. 60/652,281, filed Feb. 11, 2005.

CROSS REFERENCE TO RELATED APPLICATIONS

The present invention claims priority to U.S. Provisional Application Ser. No. 60/652,281, filed Feb. 11, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds that are useful in inducing cytokine biosynthesis in animals. Such compounds are of the following Formula I:

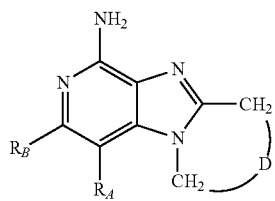

I wherein $R_A$, $R_B$, and D are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VII:

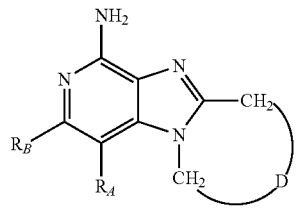

I

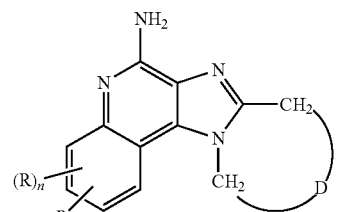

II

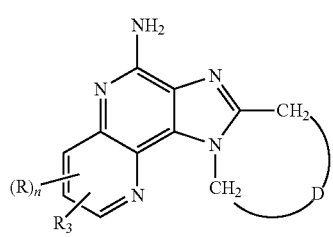

III

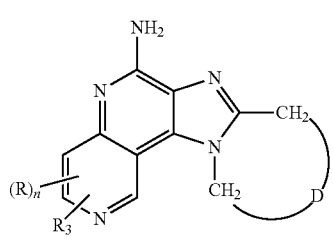

IV

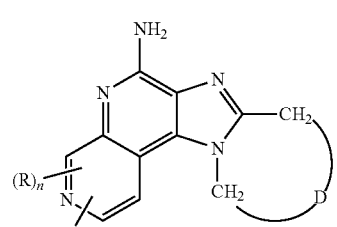

V

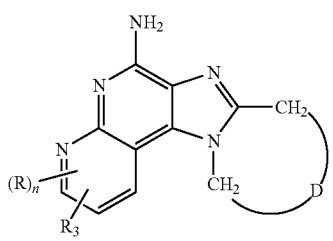

VI

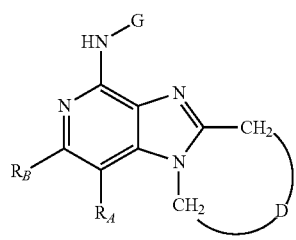

VII as well as intermediates of the following Formulas X through XV:

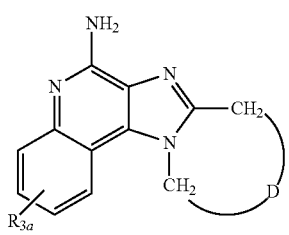

X

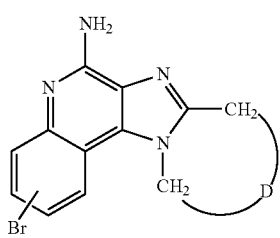

XI

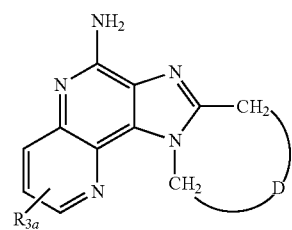

XII

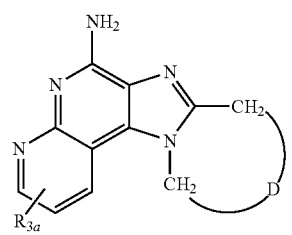

XIII

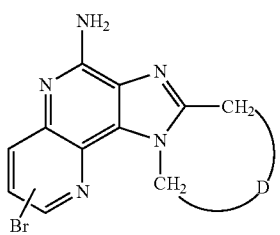

XIV

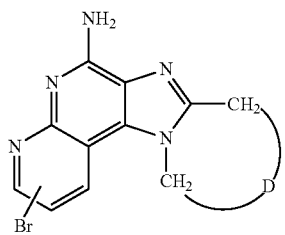

XV wherein $R_A$, $R_B$, R, $R_3$, $R_{3a}$, n, G, and D are as defined below; and pharmaceutically acceptable salts thereof.

In one embodiment, the present invention provides a compound of Formula I:

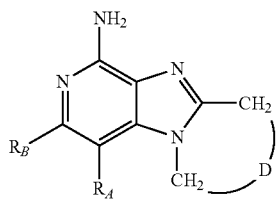

I wherein:
$R_A$ and $R_B$ taken together form a fused benzene ring or fused pyridine ring wherein the benzene ring or pyridine ring is substituted by one $R_3$ group, or substituted by one $R_3$ group and one R group;

$R_3$ is —O—$R_{3-1}$ or $R_{3-2}$;

$R_{3-1}$ is selected from the group consisting of:
—Z—Y—$R_4$,
—Z—Y—X—Y—$R_4$,
—Z—$R_5$,
—Z-Het,
—Z-HetAr,
—Z-Het'-$R_4$,
—Z-HetAr'—$R_4$,
—Z-Het'-Y—$R_4$, and
—Z-HetAr'-Y—$R_4$;

$R_{3-2}$ is selected from the group consisting of:
—Z—Y—$R_4$,
Z—Y—X—Y—$R_4$,
—Z—$R_5$,
—Z-Het,
—Z-Het'-$R_4$, and
—Z-Het'-Y—$R_4$;

R is selected from the group consisting of alkyl, alkoxy, hydroxy, halogen, and trifluoromethyl;

D is selected from the group consisting of —(CH$_2$)$_{1-4}$— and —(CH$_2$)$_c$—O—(CH$_2$)$_d$—;

wherein c and d are integers and c+d is 0 to 3;

Z is selected from the group consisting of a bond, alkylene, alkenylene, and alkynylene, wherein alkylene, alkenylene, and alkynylene can be optionally interrupted with one or more —O— groups;

Y is selected from the group consisting of:
- —O—,
- —S(O)$_{0-2}$—,
- —S(O)$_2$—N(R$_8$)—,
- —C(R$_6$)—,
- —C(R$_6$)—O—,
- —O—C(R$_6$)—,
- —O—C(O)—O—,
- —N(R$_8$)-Q-,
- —C(R$_6$)—N(R$_8$)—,
- —O—C(R$_6$)—N(R$_8$)—,
- —C(R$_6$)—N(OR$_9$)—,
- —C(=N—O—R$_9$)—,
- —CH(—N(—O—R$_8$)-Q-R$_4$)—,

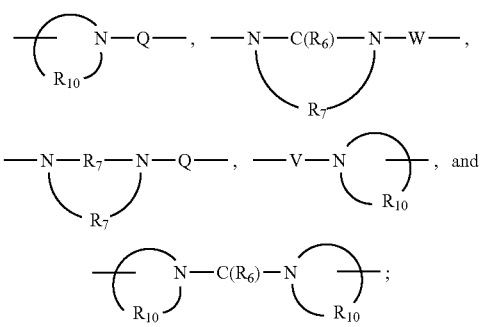

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

HetAr is heteroaryl which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

HetAr' is heteroarylene which can be unsubstituted or can be substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

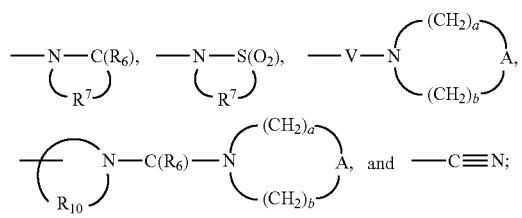

R is selected from the group consisting of =O and =S;

R$_7$ is C$_{2-7}$ alkylene;

R$_8$ is selected from the group consisting of hydrogen, alkyl, alkoxyalkylenyl, hydroxyalkylenyl, heteroarylalkylenyl, and arylalkylenyl;

R$_9$ is selected from the group consisting of hydrogen and alkyl;

R$_{10}$ is C$_{3-8}$ alkylene;

A is selected from the group consisting of —O—, —CH$_2$—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_6$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that Z is other than a bond when:

R$_3$ is —O—R$_{3-1}$, R$_{3-1}$ is —Z—Y—R$_4$ or —Z—Y—X—Y—R$_4$, and the Y group bonded to Z is —O—, —S—, —S(O)—, —O—C(R$_6$)—, —OC(O)—O—, —N(R$_8$)-Q-, —O—C(R$_6$)—N(R$_8$)—,

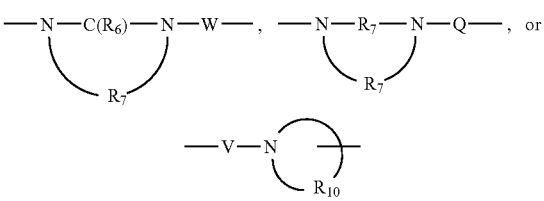

wherein V is
—O—C(R$_6$)— or —N(R$_8$)—C(R$_6$)—; or
R$_3$ is —O—R$_{3-1}$, R$_{3-1}$ is —Z—R$_5$, and R$_5$ is —C≡N,

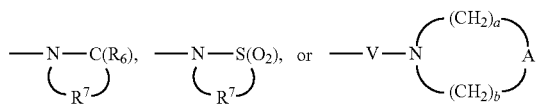

wherein V is
—O—C(R$_6$)— or —N(R$_8$)—C(R$_6$)—; or
R$_3$ is —O—R$_{3-1}$, R$_{3-1}$ is —Z-Het, —Z-Het'-R$_4$, or —Z-Het'-Y—R$_4$, and Z is attached to a nitrogen atom in Het or Het'; or
R$_3$ is R$_{3-2}$, R$_{3-2}$ is —Z—Y—R$_4$, R$_A$ and R$_B$ taken together form a fused benzene ring, and —Y—R$_4$ is alkoxy;

or a pharmaceutically acceptable salt thereof.

In another embodiment, the present invention provides a compound of Formula II:

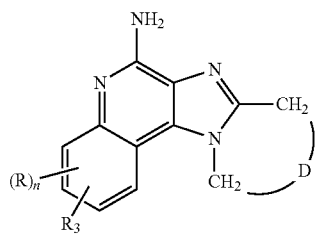

II wherein:
R$_3$ is —O—R$_{3-1}$ or R$_{3-2}$;
R$_{3-1}$ is selected from the group consisting of:
—Z—Y—R$_4$,
—Z—Y—X—Y—R$_4$,
—Z—R$_5$,
—Z-Het,
—Z-HetAr,
—Z-Het'-R$_4$,
—Z-HetAr'—R$_4$,
—Z-Het'-Y—R$_4$, and
—Z-HetAr'-Y—R$_4$;
R$_{3-2}$ is selected from the group consisting of:
—Z—Y—R$_4$,
—Z—Y—X—Y—R$_4$,
—Z—R$_5$,
—Z-Het,
—Z-Het'-R$_4$, and
—Z-Het'-Y—R$_4$;
R is selected from the group consisting of alkyl, alkoxy, hydroxy, halogen, and trifluoromethyl;
n is 0 or 1;
D is selected from the group consisting of —(CH$_2$)$_{1-4}$— and —(CH$_2$)$_c$—O—(CH$_2$)$_d$—;
wherein c and d are integers and c+d is 0 to 3;
Z is selected from the group consisting of a bond, alkylene, alkenylene, and alkynylene, wherein alkylene, alkenylene, and alkynylene can be optionally interrupted with one or more —O— groups;
Y is selected from the group consisting of:
—O—,
—S(O)$_{0-2}$—,
—S(O)$_2$—N(R$_8$)—,
—C(R$_6$)—,
—C(R$_6$)—O—,
—O—C)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—C(=N—O—R$_8$)—,
—CH(—N(—O—R$_8$)-Q-R$_4$)—,

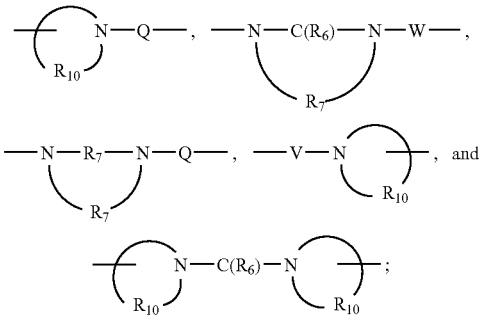

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

HetAr is heteroaryl which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

HetAr' is heteroarylene which can be unsubstituted or can be substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

$$-N(R_7)-C(R_6)-, \quad -N(R_7)-S(O_2)-, \quad -V-N\begin{pmatrix}(CH_2)_a \\ (CH_2)_b\end{pmatrix}A,$$

$$-(\ \ N(R_{10})\ \ )-C(R_6)-N\begin{pmatrix}(CH_2)_a \\ (CH_2)_b\end{pmatrix}A, \text{ and } -C\equiv N;$$

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, heteroarylalkylenyl, and arylalkylenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_9$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that Z is other than a bond when:
  $R_3$ is -Q-$R_{3-1}$, $R_{3-1}$ is —Z—Y—$R_4$ or —Z—Y—X—Y—$R_4$, and the Y group bonded to Z is —O—, —S—, —S(O)—, —O—C(R$_6$)—, —OC(O)—O—, —N(R$_8$)-Q-, —O—C(R$_6$)—N(R$_8$)—, $$-N(R_7)-C(R_6)-N-W-, \quad -N(R_7)-R_7-N-Q-, \text{ or}$$

$$-V-N(R_{10})-$$

wherein V is
  —O—C(R$_6$)— or —N(R$_9$)—C(R$_6$)—; or
$R_3$ is —O—$R_{3-1}$, $R_{3-1}$ is —Z—$R_5$, and $R_5$ is —C≡N, $$-N(R_7)-C(R_6), \quad -N(R_7)-S(O_2), \text{ or } -V-N\begin{pmatrix}(CH_2)_a \\ (CH_2)_b\end{pmatrix}A$$

wherein V is
  —O—C(R$_6$)— or —N(R$_8$)—C(R$_5$)—; or
$R_3$ is —O—$R_{3-1}$, $R_{3-1}$ is —Z-Het, —Z-Het'-R$_4$, or —Z-Het'-Y—R$_4$, and Z is attached to a nitrogen atom in Het or Het'; or $R_3$ is $R_{3-2}$, $R_{3-2}$ is —Z—Y—R$_4$, and —Y—R$_4$ is alkoxy;
or a pharmaceutically acceptable salt thereof.

In another embodiment, the present invention provides a compound selected from the group consisting Formulas III, IV, V, and VI:

III

IV

V, and

VI wherein:
$R_3$ is —O—$R_{3-1}$ or $R_{3-2}$;
$R_{3-1}$ is selected from the group consisting of:
  —Z—Y—R$_4$,
  —Z—Y—X—Y—R$_4$,
  —Z—R$_5$,
  —Z-Het,
  —Z-HetAr,
  —Z-Het'-R$_4$,
  —Z-HetAr'—R$_4$,
  —Z-Het'-Y—R$_4$, and
  —Z-HetAr'-Y—R$_4$;
$R_{3-2}$ is selected from the group consisting of:
  —Z—Y—R$_4$,
  —Z—Y—X—Y—R$_4$,
  —Z—R$_5$,
  —Z-Het,
  —Z-Het'-R$_4$, and
  —Z-Het'-Y—R$_4$;
R is selected from the group consisting of alkyl, alkoxy, hydroxy, halogen, and trifluoromethyl; and n is 0 or 1.

D is selected from the group consisting of —$(CH_2)_{1-4}$— and —$(CH_2)_c$—O—$(CH_2)_d$—;

wherein c and d are integers and c+d is 0 to 3;

Z is selected from the group consisting of a bond, alkylene, alkenylene, and alkynylene, wherein alkylene, alkenylene, and alkynylene can be optionally interrupted with one or more —O— groups;

Y is selected from the group consisting of:
—O—,
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
$N(R_8)$-Q-,
—$C(R_6)$—$N(R_8)$—,
—O—$C(R_6)$—$N(R_8)$—,
—$C(R_6)$—$N(OR_9)$—,
—C(=O—N—O—$R_9$)—,
—CH(—N(—O—$R_8$)-Q-$R_4$)—,

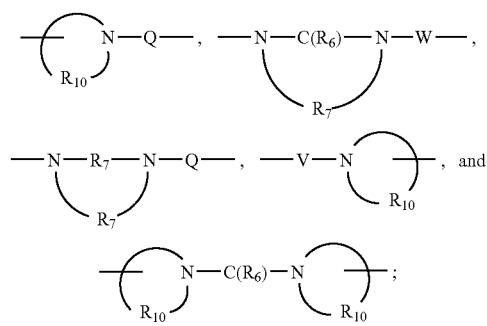

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

HetAr is heteroaryl which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

HetAr' is heteroarylene which can be unsubstituted or can be substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

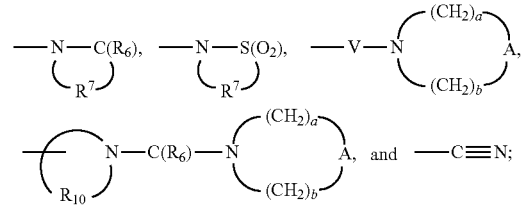

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, heteroarylalkylenyl, and arylalkylenyl;

$R_9$ is selected from the group consisting of hydrogen and alkyl;

$R_{10}$ is $C_{3-8}$ alkylene;

A is selected from the group consisting of —O—, —$CH_2$—, —C(O)—, —$S(O)_{0-2}$—, and —$N(R_4)$—;

Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, and —$C(R_6)$—$N(OR_9)$—;

V is selected from the group consisting of —$C(R_6)$—, —O—$C(R_6)$—, —$N(R_8)$—$C(R_6)$—, and —$S(O)_2$—;

W is selected from the group consisting of a bond, —C(O)—, and —$S(O)_2$—; and a and b are independently integers from 1 to 6 with the proviso that a+b is ≦7;

with the proviso that Z is other than a bond when:

$R_3$ is —O—$R_{3-1}$, $R_{3-1}$ is —Z—Y—$R_4$ or —Z—Y—X—Y—$R_4$, and the Y group bonded to Z is —O—, —S—, —S(O)—, —O—$C(R_6)$—, —OC(O)—O—, —$N(R_8)$-Q-, —O—$C(R_6)$—$N(R_8)$—,

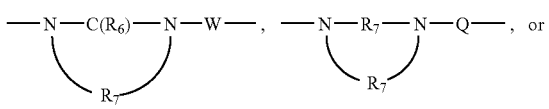

-continued

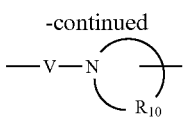

wherein V is
—O—C(R$_6$)— or —N(R$_8$)—C(R$_6$)—; or
R$_3$ is —O—R$_{3-1}$, R$_{3-1}$ is —Z—R$_5$, and R$_5$ is —C≡N,

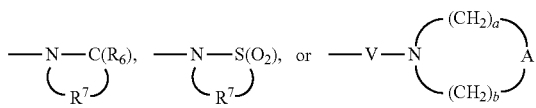

wherein V is
—O—C(R$_6$)— or —N(R$_8$)—C(R$_6$)—; or
R$_3$ is —O—R$_{3-2}$, R$_{3-2}$ is —Z-Het, —Z-Het'-R$_4$, or —Z-Het'-Y—R$_4$, and Z is attached to a nitrogen atom in Het or Het';
or a pharmaceutically acceptable salt thereof.

In another embodiment, the present invention provides a compound of Formula VII, which is a prodrug:

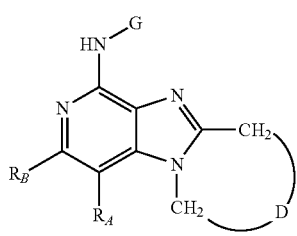

wherein:
G is selected from the group consisting of:
—C(O)—R',
α-aminoacyl,
α-aminoacyl-α-aminoacyl,
—C(O)—O—R',
—C(O)—N(R")R',
—C(—NY$_1$)—R',
—CH(OH)—C(O)—OY$_1$,
—CH(OC$_{1-4}$ alkyl)Y$_0$,
—CH$_2$Y$_2$, and
—CH(CH$_3$)Y$_2$;
R' and R" are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;
α-aminoacyl is an α-aminoacyl group derived from an α-amino acid selected from the group consisting of racemic, D-, and L-amino acids;
Y$_1$ is selected from the group consisting of hydrogen, C$_{1-6}$ alkyl, and benzyl;
Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl;

Y$_2$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl; and
R$_A$, R$_B$, and D are defined as in Formula I above;
or a pharmaceutically acceptable salt thereof.

In one embodiment, the present invention provides an intermediate compound of Formula X:

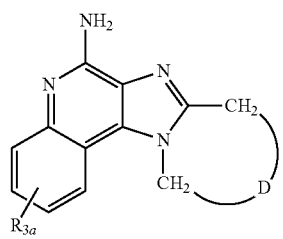

wherein:
R$_{3a}$ is benzyloxy;
R$_{3a}$ is at the 7- or 8-position; and
D is selected from the group consisting of —(CH$_2$)$_{1-4}$— and —(CH$_2$)$_c$—O—(CH$_2$)$_d$—;
wherein c and d are integers and c+d is 0 to 3;
or a pharmaceutically acceptable salt thereof.

In another embodiment, the present invention provides an intermediate compound of the Formula XI:

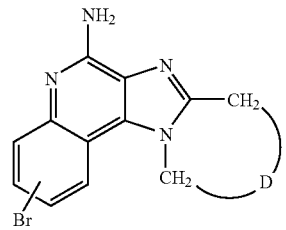

wherein:
Br is at the 7- or 8-position; and
D is selected from the group consisting of —(CH$_2$)$_{1-4}$— and —(CH$_2$)$_c$—O—(CH$_2$)$_d$—;
wherein c and d are integers and c+d is 0 to 3;
or a pharmaceutically acceptable salt thereof.

In another embodiment, the present invention provides an intermediate compound selected from the group consisting of the Formulas XII and XIII:

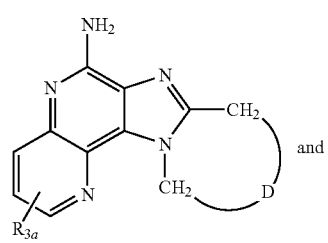

and

-continued

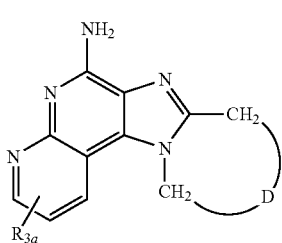

XIII wherein:
R$_{3a}$ is benzyloxy;
R$_{3a}$ is at the 7- or 8-position; and
D is selected from the group consisting of —(CH$_2$)$_{1-4}$— and —(CH$_2$)$_c$—O—(CH$_2$)$_d$—;
wherein c and d are integers and c+d is 0 to 3;
or a pharmaceutically acceptable salt thereof.

In another embodiment, the present invention provides an intermediate compound selected from the group consisting of the Formulas XIV and XV:

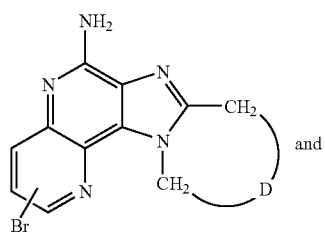

XIV and

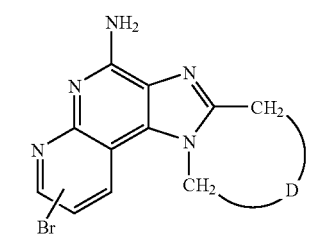

XV wherein:
Br is at the 7- or 8-position; and
D is selected from the group consisting of —(CH$_2$)$_{1-4}$— and —(CH$_2$)$_c$—O—(CH$_2$)$_d$—;
wherein c and d are integers and c+d is 0 to 3;
or a pharmaceutically acceptable salt thereof.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R$_8$)—C(R$_6$)—N(R$_8$)— each R$_8$ group is independently selected. In another example, when two Y groups are present, each Y group is independently selected. In a further example, when more than one Y group is present and each Y group contains one or more $R_8$ groups, then each Y group is independently selected, and each $R_8$ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Z, X, Y, R, $R_3$, Q, G, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formulas I or VII, $R_A$ and $R_B$ are taken together to form a fused benzene ring wherein the benzene ring is substituted by one $R_3$ group, or substituted by one $R_3$ group and one R group. In certain of these embodiments, the fused benzene ring is substituted by one $R_3$ group.

For certain embodiments of Formulas I or VII, $R_A$ and $R_B$ are taken together to form a fused pyridine ring wherein the pyridine ring is substituted by one $R_3$ group, or substituted by one $R_3$ group and one R group. In certain of these embodiments, the fused pyridine ring is substituted by one $R_3$ group.

For certain embodiments, the compound selected from the group consisting of Formulas III, IV, V, and VI, or a pharmaceutically acceptable salt thereof is the compound of Formula III:

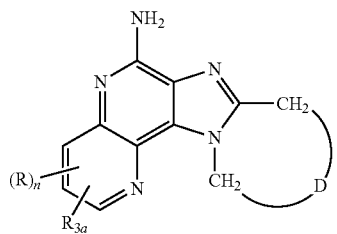

or a pharmaceutically acceptable salt thereof.

For certain embodiments, n is 0 in the above embodiments of Formulas II, III, IV, V, or VI.

For certain embodiments, including any one of the above embodiments where R is present, R is selected from the group consisting of alkyl, alkoxy, hydroxy, halogen, and trifluoromethyl.

For certain embodiments, including any one of the above embodiments where R is present, R is bromine.

For certain embodiments, including any one of the above embodiments, $R_3$ is —O—$R_{3-1}$ or $R_{3-2}$; wherein $R_{3-1}$ is selected from the group consisting of —Z—Y—$R_4$, —Z—Y—X—Y—$R_4$, —Z—$R_5$, —Z-Het, —Z-HetAr, —Z-Het'-$R_4$, —Z-HetAr'—$R_4$, —Z-Het'-Y—$R_4$, and —Z-HetAr'-Y—$R_4$; and $R_{3-2}$ is selected from the group consisting of —Z—Y—$R_4$, —Z—Y—X—Y—$R_4$, —Z—$R_5$, —Z-Het, —Z-Het'-$R_4$, and —Z-Het'-Y—$R_4$.

For certain embodiments, including any one of the above embodiments, $R_3$ is —O—Z—Y—$R_4$, —O—Z—Y—X—Y—$R_4$, —Z—Y—$R_4$, or —Z—Y—X—Y—$R_4$.

For certain embodiments, including any one of the above embodiments, Y is selected from the group consisting of —C($R_6$)—, —C($R_6$)—N($R_8$)—, —N($R_8$)-Q-, and

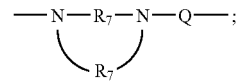

wherein Q is selected from the group consisting of a bond, —C(O)—, —C(O)—O—, —S(O)$_2$—, —C($R_6$)—N($R_8$)—; $R_6$ is selected from the group consisting of =O or =S; $R_8$ is selected from the group consisting of hydrogen, $C_{1-4}$ alkyl, and alkoxyalkylenyl; and each $R_7$ is independently selected from $C_{2-3}$ alkylene; and $R_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents. For certain of these embodiments, Y is —N($R_8$)-Q- wherein $R_8$ is hydrogen, Q is —S(O)$_2$—, —C(O)—, or —C(O)—NH—, and $R_4$ is $C_{1-3}$ alkyl or pyridyl. For certain of these embodiments, Y is —NH—S(O)$_2$— and $R_4$ is methyl, or Y is —NH—C(O)— and $R_4$ is 3-pyridyl, or Y is —NH—C(O)—NH— and $R_4$ is isopropyl. For certain of these embodiments, Y is —C(O)— and $R_4$ is heterocyclyl. For certain of these embodiments, heterocyclyl is selected from the group consisting of pyrrolidinyl, piperidinyl, thiazolidinyl, aziridinyl, azepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and piperazinyl.

For certain embodiments, including any one of the above embodiments not excluding this definition, $R_3$ is —Z—Y—$R_4$. For certain of these embodiments, Z is a bond, and Y is —O—. For certain of these embodiments, $R_4$ is arylalkylenyl which is unsubstituted or substituted by one or more substitutents independently selected from the group consisting of halogen, cyano, $C_{1-4}$ alkoxy. For certain of these embodiments, arylalkylenyl is benzyl, 1-phenylethyl, or 4-phenylbutyl. For certain of these embodiments, arylalkylenyl is benzyl which is unsubstituted or substituted by one or more halogen groups. For certain of these embodiments, halogen is fluoro.

For certain embodiments, including any one of the above embodiments not excluding this definition, $R_3$ is —O—Z—Y—$R_4$. For certain of these embodiments, Z is alkylene, and Y is —O—, —C(O)—NH—, C(O)—O—, C(O)—, S(O)$_2$—, or —N($R_8$)-Q-. For certain of these embodiments, $R_4$ is hydrogen, alkyl, aryl, or arylalkylenyl wherein aryl and arylalkylenyl are unsubstituted or substituted by one or more substituents independently selected from the group consisting of alkyl, alkoxy, and halogen.

For certain embodiments, including any one of the above embodiments not excluding this definition, $R_3$ is —Z—Y—X—Y—$R_4$. For certain of these embodiments, Z is a bond. For certain of these embodiments the Y bonded to Z is —O—. For certain of these embodiments, X is alkylene-arylene. For certain of these embodiments, X is methylene-phenylene. For certain of these embodiments, the Y bonded to $R_4$ is —C(O)—O—. For certain of these embodiments, $R_4$ is $C_{1-4}$ alkyl. Alternatively, for certain of these embodiments, X is propylene-piperidin-1,4-diyl. For certain of these embodiments, the Y bonded to R is —C(O)—NH—. For certain of these embodiments, R is hydrogen.

For certain embodiments, including any one of the above embodiments not excluding this definition, $R_3$ is —O—Z—$R_5$ or —Z—$R_5$. For certain of these embodiments, $R_5$ is selected from the group consisting of:

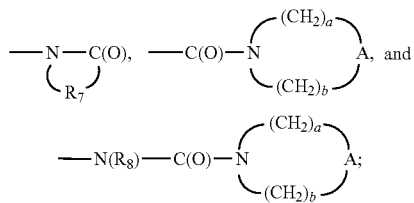

wherein A is selected from the group consisting of —O—, —S—, and —SO$_2$—; $R_7$ is $C_{2-4}$ alkylene; $R_9$ is selected from the group consisting of hydrogen and $C_{1-4}$ alkyl; and a and b are each independently an integer of 1 to 3; with the proviso that Z in —O—Z—$R_5$ is other than a bond when $R_5$ is

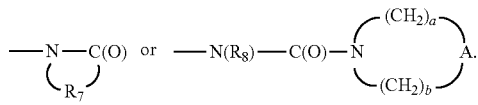

For certain embodiments, $R_3$ is —O—Z—$R_5$. For certain of these embodiments, $R_5$ is

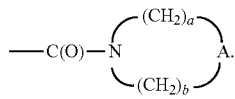

For certain of these embodiments, A is —O—, and a and b are each 2. For certain of these embodiments, Z is alkylene. For certain of these embodiments, Z is $C_{1-6}$ alkylene. Alternatively, for certain of these embodiments where $R_3$ is —O—Z—$R_5$, Z is alkylene, and $R_5$ is —C≡N.

For certain embodiments, $R_3$ is —Z—$R_5$, and $R_5$ is —C≡N. In certain of these embodiments, Z is other than a bond. In certain of these embodiments, $R_3$ is —CH═CH—C≡N.

For certain embodiments, including any one of the above embodiments not excluding this definition, $R_3$ is —O—Z-Het, —O—Z-Het'-$R_4$, —Z-Het, or —Z-Het'-$R_4$. For certain of these embodiments, Het and Het' are, respectively, selected from the group consisting of the monovalent and divalent forms of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents. For certain of these embodiments, Het and Het' are, respectively, selected from the group consisting of the monovalent and divalent forms of pyrrolidinyl, piperidinyl, morpholinyl, and thiomorpholinyl, each of which is unsubstituted or substituted by one or more substitutents. For certain of these embodiments, Het is substituted by one or more substituents selected from the group consisting of alkyl, hydroxyl, hydroxyalkyl, hydroxyalkyleneoxyalkylenyl, and dialkylamino. For certain of these embodiments, $R_4$ is heterocyclyl.

For certain embodiments, including any one of the above embodiments not excluding this definition, $R_3$ is —O—Z-Het. For certain of these embodiments, Z is a bond or alkylene with the proviso that when Z is attached to a nitrogen atom in Het, then Z is alkylene. For certain of these embodiments, Het is tetrahydrofuranyl which is unsubstituted or substituted by one or more substituents independently selected from the group consisting of alkyl and oxo. For certain of these embodiments, Z is $C_{1-6}$ alkylene.

For certain embodiments, including any one of the above embodiments not excluding this definition, $R_3$ is —O—Z-HetAr or —O—Z-HetAr'—$R_4$. For certain of these embodiments, HetAr and HetAr' are, respectively, selected from the group consisting of the monovalent and divalent forms of benzothiazolyl, furanyl, imidazolyl, indolyl, isoxazolyl, oxadiazolyl, pyrazinyl, pyridinyl, pyrrolyl, and thiazolyl. For certain of these embodiments, HetAr and HetAr' are, respectively, selected from the group consisting of the monovalent and divalent forms of thiazolyl, imidazolyl, isoxazolyl, and pyridinyl. For certain of these embodiments, $R_3$ is —O—Z-HetAr. For certain of these embodiments, Z is alkylene. For certain of these embodiments, Z is $C_{1-6}$ alkylene. For certain of these embodiments, HetAr is pyridinyl, pyrrolyl, or thiazolyl. For certain of these embodiments, HetAr is pyrrolyl or thiazolyl.

For certain embodiments, $R_3$ is —Z-Het'-Y—$R_4$. For certain of these embodiments, —Y—$R_4$ is selected from the group consisting of —C(O)-alkyl, —C(O)—O—H, —C(O)—O-alkyl, —C(O)—NH$_2$—, —C(O)—NH-alkyl, and —NH—C(O)-alkyl.

For certain embodiments, including any one of the above embodiments where this definition is not excluded, Z is alkylene optionally interrupted with one or more —O— groups. For certain of these embodiments, Z is alkylene. In certain of these embodiments, Z is $C_{1-6}$ alkylene.

For certain embodiments, including any of the above embodiments where $R_3$ is present, $R_3$ is at the 7-position.

For certain embodiments, $R_{3a}$ is benzyloxy.

For certain embodiments, $R_{3a}$ is at the 7- or 8-position.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.

For certain embodiments, $R_4$ is heterocyclyl.
For certain embodiments, $R_4$ is heteroaryl.
For certain embodiments, $R_4$ is 3-pyridyl.
For certain embodiments, $R_4$ is $C_{1-3}$ alkyl or pyridyl.
For certain embodiments, $R_4$ is hydrogen or alkyl.
For certain embodiments, $R_4$ is alkyl.
For certain embodiments, $R_4$ is $C_{1-4}$ alkyl.
For certain embodiments, $R_4$ is isopropyl.
For certain embodiments, $R_4$ is methyl.
For certain embodiments, $R_4$ is hydrogen.

For certain embodiments, $R_5$ is selected from the group consisting of:

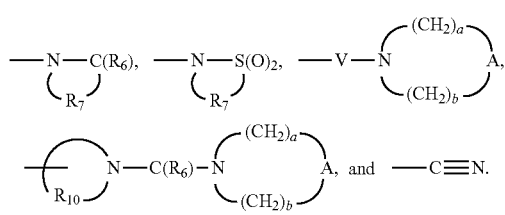

For certain embodiments, $R_5$ is selected from the group consisting of:

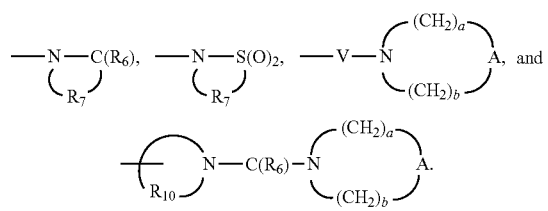

For certain embodiments, $R_5$ is selected from the group consisting of

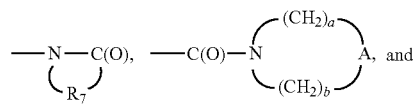

-continued

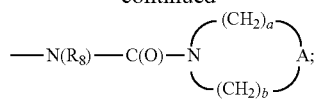

wherein A is selected from the group consisting of —O—, —S—, and —SO$_2$—; $R_7$ is $C_{2-4}$ alkylene; $R_5$ is selected from the group consisting of hydrogen and $C_{1-4}$ alkyl; and a and b are each independently an integer of 1 to 3; with the proviso that Z in —O—Z—R$_5$ is other than a bond when $R_5$ is

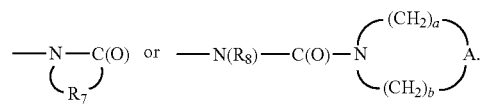

In certain of these embodiments a and b are each 2.

For certain of these embodiments, $R_5$ is

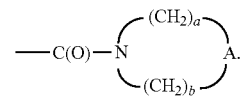

For certain embodiments, $R_6$ is selected from the group consisting of =O and =S.
For certain embodiments, $R_6$ is =O.
For certain embodiments, $R_7$ is $C_{2-7}$ alkylene.
For certain embodiments, $R_7$ is $C_{2-4}$ alkylene.
For certain embodiments, $R_7$ is selected from $C_{2-3}$ alkylene.
For certain embodiments, $R_8$ is selected from the group consisting of hydrogen, alkyl, hydroxyalkylenyl, alkoxyalkylenyl, arylalkylenyl, and heteroarylalkylenyl.
For certain embodiments, $R_8$ is selected from the group consisting of hydrogen, $C_{1-4}$ alkyl, and $C_{1-4}$ alkoxyC$_{1-4}$ alkylenyl.
For certain embodiments, $R_8$ is hydrogen or $C_{1-4}$ alkyl.
For certain embodiments, $R_8$ is $C_{1-4}$ alkyl.
For certain embodiments, $R_8$ is hydrogen.
For certain embodiments, $R_9$ is selected from the group consisting of hydrogen and alkyl.
For certain embodiments, $R_{10}$ is $C_{3-8}$ alkylene.
For certain embodiments, $R_{10}$ is $C_{4-6}$ alkylene.
For certain embodiments, D is selected from the group consisting of —(CH$_2$)$_{1-4}$— and —(CH$_2$)$_c$—O—(CH$_2$)$_d$—; wherein c and d are integers and c+d is 0 to 3.
For certain embodiments, D is selected from the group consisting of —(CH$_2$)$_{1-4}$— and —(CH$_2$)$_c$—O—(CH$_2$)$_d$—; wherein c and d are integers and c+d is 1 to 3.

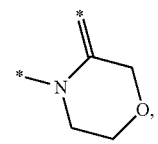

For certain embodiments, D is —CH$_2$—O—, and the ring containing D is the bonds with * being part of the imidazo ring.

For certain embodiments, A is selected from the group consisting of —O—, —CH$_2$—, —C(O)—, —S(O)$_{0-2}$—, and —N(R$_4$)—.

For certain embodiments, A is —O—, —S—, or —SO$_2$—.
For certain embodiments, A is —O— or —S(O)$_2$—.
For certain embodiments, A is —O—.

For certain embodiments, including any one of the above embodiments of Formula VII, G is selected from the group consisting of —C(O)—R', α-aminoacyl, α-aminoacyl-α-aminoacyl, —C(O)—O—R', —C(O)—N(R")R', —C(=NY$_1$)—R', —CH(OH)—C(O)—OY$_1$, —CH(OC$_{1-4}$ alkyl)Y$_0$, —CH$_2$Y$_2$, and —CH(CH$_3$)Y$_2$. For certain of these embodiments, R' and R" are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)—NH$_2$, with the proviso that R" can also be hydrogen; α-aminoacyl is an α-aminoacyl group derived from an α-amino acid selected from the group consisting of racemic, D-, and L-amino acids; Y$_1$ is selected from the group consisting of hydrogen, C$_{1-6}$ alkyl, and benzyl; Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_2$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula VII, G is selected from the group consisting of —C(O)—R', α-aminoacyl, and —C(O)—O—R'.

For certain embodiments, including any one of the above embodiments of Formula VII, G is selected from the group consisting of —C(O)—R', α-amino-C$_{2-11}$ acyl, and —C(O)—O—R'. α-Amino-C$_{2-11}$ acyl includes α-amino acids containing a total of at least 2 carbon atoms and a total of up to 11 carbon atoms, and may also include one or more heteroatoms selected from the group consisting of O, S, and N. For certain of these embodiments, R' contains one to ten carbon atoms.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the α-amino acid is selected from the group consisting of racemic, D-, and L-amino acids.

In certain embodiments, Q is selected from the group consisting of a bond, —C(R$_8$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In certain embodiments, Q is selected from the group consisting of —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

In certain embodiments, Q is other than a bond when R$_3$ is —Z—Y—R$_4$, Z is a bond, and Y is —N(R$_8$)-Q-.

In certain embodiments, Q is selected from the group consisting of a bond, —C(O)—, —C(O)—O—, —S(O)$_2$—, and —C(R$_6$)—N(R$_8$)—.

In certain embodiments, Q is —S(O)$_2$—, —C(O)—, or —C(O)—NH—.

In certain embodiments, Q is —C(O)—.
In certain embodiments, Q is —S(O)$_2$—.
In certain embodiments, Q is —C(R$_6$)—N(R$_8$)—.
In certain embodiments, Q is a bond.

In certain embodiments, V is selected from the group consisting of —C(R$_6$)—, —O—C(R$_6$)—, —N(R$_9$)—C(R$_6$)—, and —S(O)$_2$—.

In certain embodiments, V is selected from the group consisting of —C(O)— and —N(R$_8$)—C(O)—.

In certain embodiments, W is selected from the group consisting of a bond, —C(O)—, and —S(O)$_2$—

In certain embodiments, W is a bond or —C(O)—.

In certain embodiments, W is a bond.

In certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

In certain embodiments, X is alkylene terminated with arylene. For certain of these embodiments, X is methylenephenylene.

In certain embodiments, X is alkylene terminated with heterocyclylene. For certain of these embodiments, X is propylene-piperidin-1,4-diyl.

In certain embodiments, Y is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—, —O—N(R$_8$)-Q-, —O—N=C(R$_4$)—, —C(=N—O—R$_8$)—, —CH(—N(—O—R$_8$)-Q-R$_4$)—,

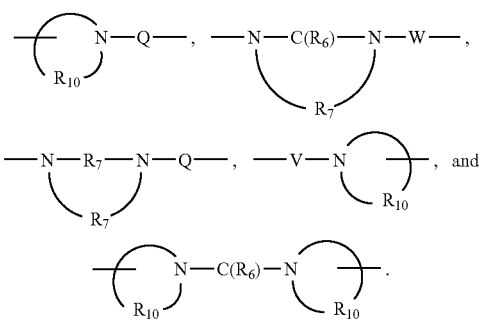

In certain of these embodiments, including any one of the above embodiments wherein Y is present, Y is other than —O—.

In certain embodiments, Y is selected from the group consisting of —C(R$_6$)—, —C(R$_6$)—N(R$_8$)—, —N(R$_8$)-Q-, and

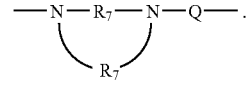

In certain of these embodiments, Q is selected from the group consisting of a bond, —C(O)—, —C(O)—O—, —S(O)₂—, -and —C(R₆)—N(R₈)—; R₆ is selected from the group consisting of =O and =S; R₈ is selected from the group consisting of hydrogen, C₁₋₄ alkyl, and C₁₋₄ alkoxyC₄ alkylenyl; and each R₇ is independently selected from C₂₋₃ alkylene.

In certain embodiments, Y is —N(R₈)-Q-.

In certain embodiments, Y is —NH—S(O)₂—.

In certain embodiments, Y is selected from the group consisting of —C(O)—, —C(O)—O—, —C(O)—NH—, and —NH—C(O)—.

In certain embodiments, Y is selected from the group consisting of —O—, —C(O)—, —C(O)—O—, —C(O)—NH—, —S(O)₂—, and —N(R₈)-Q-.

In certain embodiments, Y is —C(O)—.

In certain embodiments, Y is —NH—C(O)—.

In certain embodiments, Y is —NH—C(O)—NH—.

In certain embodiments, Y is —O—.

In certain embodiments, Z is selected from the group consisting of a bond, alkylene, alkenylene, and alkynylene, wherein alkylene, alkenylene, and alkynylene can be optionally interrupted with one or more —O— groups; with the proviso that Z is other than a bond when:
R₃ is —O—R₃₋₁, R₃₋₁ is —Z—Y—R₄ or —Z—Y—X—Y—R₄, and the Y group bonded to Z is —O—, —S—, —S(O)—, —O—C(R₆)—, —OC(O)—O—, —N(R₈)-Q-, —O—C(R₆)—N(R₈)—,

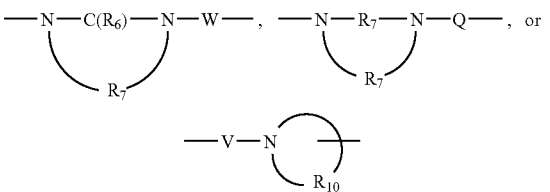

wherein V is
—O—C(R₆)— or —N(R₈)—C(R₆)—; or
R₃ is —O—R₃₋₁, R₃₋₁ is —Z—R₅, and R₅ is C≡N,

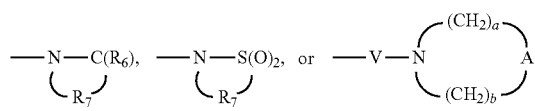

wherein V is
—O—C(R₆)— or —N(R₈)—C(R₆)—; or
R₃ is —O—R₃₋₂, R₃₋₂ is —Z-Het, —Z-Het'-R₄, or —Z-Het'-Y—R₄, and Z is attached to a nitrogen atom in Het or Het'. In certain of these embodiments, Z is other than a bond further when R₃ is —Z—R₅, and R₅ is —C≡N. In certain of these embodiments, Z is other than a bond further when R₃ is —Z—Y—R₄, Y is —C(O)— or —C(O)—O—, and R₄ is alkyl.

In certain embodiments, Z is alkylene optionally interrupted with one or more —O— groups.

In certain embodiments, Z is C₁₋₆ alkylene.

In certain embodiments, Z is a bond.

In certain embodiments, Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

In certain embodiments, Het is selected from the group consisting of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents.

In certain embodiments, Het is selected from the group consisting of pyrrolidinyl, piperidinyl, and morpholinyl, each of which is unsubstituted or substituted by one or more substituents.

In certain embodiments, Het is substituted by one or more substituents selected from the group consisting of alkyl, hydroxyl, hydroxyalkyl, hydroxyalkyleneoxyalkylenyl, and dialkylamino.

In certain embodiments, Het is unsubstituted.

In certain embodiments, Het is tetrahydrofuranyl which is unsubstituted or substituted by one or more substituents independently selected from the group consisting of alkyl and oxo.

In certain embodiments, Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo.

In certain embodiments, Het' is selected from the group consisting of the divalent forms of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substituents.

In certain embodiments, Het' is selected from the group consisting of the divalent forms of pyrrolidinyl, piperidinyl, and morpholinyl, each of which is unsubstituted or substituted by one or more substituents.

In certain embodiments, Het' is unsubstituted (except by —R₄ or —Y—R₄).

For certain embodiments, HetAr is heteroaryl which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino.

For certain embodiments, HetAr is selected from the group consisting of benzothiazolyl, furanyl, imidazolyl, indolyl, isoxazolyl, oxadiazolyl, pyrazinyl, pyridinyl, pyrrolyl, and thiazolyl.

For certain embodiments, HetAr is pyridinyl, pyrrolyl, or thiazolyl.

For certain embodiments, HetAr' is heteroarylene which can be unsubstituted or can be substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino.

For certain embodiments, HetAr' is selected from the group consisting of the divalent forms of benzothiazolyl, furanyl, imidazolyl, indolyl, isoxazolyl, oxadiazolyl, pyrazinyl, pyridinyl, pyrrolyl, and thiazolyl.

For certain embodiments, a and b are independently integers from 1 to 6 with the proviso that a+b is ≦7.

For certain embodiments, a and b are each independently 1 to 3.

For certain embodiments, a and b are each 2.

For certain embodiments, n is 0 or 1.

For certain embodiments, n is 0.

For certain embodiments of Formulas X, XI, XII, XIII, XIV, or XV, D is selected from the group consisting of —(CH$_2$)$_{1-4}$— and —(CH$_2$)$_c$—O—(CH$_2$)$_d$—; wherein c and d are integers and c+d is 1 to 3.

For certain embodiments of Formulas X, XI, XII, XIII, XIV, or XV, D is —CH$_2$—O—, and the ring containing D is

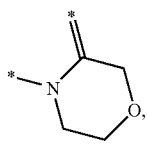

the bonds with * being part of the imidazo ring.

For certain embodiments, Formula XI is a compound selected from the group consisting of:

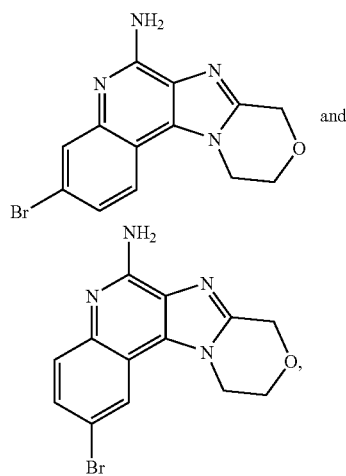

or a pharmaceutically acceptable salt thereof.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography, recrystallization, and differential (i.e., liquid-liquid) extraction techniques.

Compounds of the invention can be prepared according to Reaction Scheme I, wherein R, R$_{3-1}$, c, d, and n are as defined above; Hal is chloro, bromo, or iodo; E is carbon (imidazoquinolines) or nitrogen (imidazonaphthyridines); Bn is benzyl; and P is a hydroxy protecting group. In step (1) of Reaction Scheme I, a benzyloxyaniline or benzyloxyaminopyridine of Formula LV is treated with the condensation product generated from 2,2-dimethyl-1,3-dioxane-4,6-dione (Meldrum's acid) and triethyl orthoformate to provide an imine of Formula LVI. The reaction is conveniently carried out by adding a solution of a compound of Formula LV to a heated mixture of Meldrum's acid and triethyl orthoformate and heating the reaction at an elevated temperature such as 45° C. The product can be isolated using conventional methods. Many anilines and aminopyridines of Formula LV are commercially available; others can be prepared by known synthetic methods. For example, benzyloxy-pyridines of Formula LV can be prepared using the method of Holladay et al., *Biorg. Med. Chem. Lett.*, 8, pp. 2797-2802, (1998).

In step (2) of Reaction Scheme I, an imine of Formula LVI undergoes thermolysis and cyclization to provide a compound of Formula XVII. The reaction is conveniently carried out in a medium such as DOWTHERM A heat transfer fluid at a temperature in the range of 200 to 250° C. The product can be isolated using conventional methods.

In step (3) of Reaction Scheme I, a compound of Formula XVII is nitrated under conventional nitration conditions to provide a benzyloxy-3-nitroquinolin-4-ol of Formula XVIII. The reaction is conveniently carried out by adding nitric acid to the compound of Formula XVII in a suitable solvent such as propionic acid and heating the mixture at an elevated temperature such as 125° C. The product can be isolated using conventional methods.

In step (4) of Reaction Scheme I, a benzyloxy-3-nitroquinolin-4-ol or benzyloxy-3-nitro[1,5]naphthyridin-4-ol of Formula XVIII is chlorinated using conventional chlorination chemistry to provide a benzyloxy-4-chloro-3-nitroquinoline or benzyloxy-4-chloro-3-nitro[1,5]naphthyridine of Formula XIX. The reaction is conveniently carried out by treating the compound of Formula XVIII with phosphorous oxychloride in a suitable solvent such as DMF. The reaction can be carried out at an elevated temperature such as 100° C., and the product can be isolated using conventional methods.

In step (5) of Reaction Scheme I, a benzyloxy-4-chloro-3-nitroquinoline or benzyloxy-4-chloro-3-nitro[1,5]naphthyridine of Formula XIX is treated with an amino alcohol of formula HO—$(CH_2)_c$—$CH_2$—$NH_2$ to provide a benzyloxy-3-nitroquinolin-4-amine or benzyloxy-3-nitro[1,5]naphthyridin-4-amine of Formula XX. The reaction is conveniently carried out by adding the amino alcohol of formula HO—$(CH_2)_c$—$CH_2$—$NH_2$ to a solution of a compound of Formula XIX in a suitable solvent such as dichloromethane in the presence of a tertiary amine such as triethylamine. The reaction can be carried out at ambient temperature or at an elevated temperature such as, for example, the reflux temperature of the solvent. The reaction product can be isolated using conventional methods.

In step (6) of Reaction Scheme I, the hydroxy group of a 3-nitroquinolin-4-amine or 3-nitro[1,5]naphthyridin-4-amine of Formula XX is protected using conventional techniques to provide a 3-nitroquinolin-4-amine or 3-nitro[1,5]naphthyridin-4-amine of Formula XXI. A number of suitable protecting groups can be used; in particular, protecting groups that would survive the reduction in step (7) are preferred. Suitable protecting groups include but are not limited to silyl groups such as the tert-butyl dimethylsilyl group. The reaction is conveniently carried out by treating the hydroxy-substituted compound of Formula XX with tert-butyldimethylsilyl chloride in the presence of a base such as triethylamine and catalytic 4-(dimethylamino)pyridine (DMAP). The reaction can be carried out in a suitable solvent such as pyridine or dichloromethane at an elevated temperature such as 60° C. The product can be isolated by conventional methods. Compounds of Formula XXI may also be prepared in step (5) of Reaction Scheme I if the hydroxy group on a compound of formula HO—$(CH_2)_c$—$CH_2$—$NH_2$ is protected before the reaction.

In step (7) of Reaction Scheme I, a 3-nitroquinolin-4-amine or 3-nitro[1,5]naphthyridin-4-amine of Formula XXI is reduced to provide a quinoline-3,4-diamine or [1,5]naphthyridine-3,4-diamine of Formula XXII. The reaction can be carried out by hydrogenation using a heterogeneous hydrogenation catalyst such as platinum on carbon. The hydrogenation is conveniently carried out in a Parr apparatus in a suitable solvent such as toluene, methanol, or acetonitrile. The reaction can be carried out at ambient temperature, and the product can be isolated using conventional methods.

In step (8) of Reaction Scheme I, a quinoline-3,4-diamine or [1,5]naphthyridine-3,4-diamine of Formula XXII is reacted with a carboxylic acid equivalent, which is selected such that it will provide the desired —$CH_2$—$(CH_2)_d$-Hal substituent in a 1H-imidazo[4,5-c]quinoline or 1H-imidazo[4,5-c][1,5]naphthyridine of Formula XXIII. Suitable carboxylic acid equivalents include ortho esters, acid halides, and imidates or salts thereof.

When the carboxylic acid equivalent is an imidate of formula Hal-$(CH_2)_d$—$CH_2$—C(=NH)—O-alkyl or a salt thereof, the reaction is conveniently carried out by combining a quinoline-3,4-diamine or [1,5]naphthyridine-3,4-diamine of Formula XXII with the imidate in a suitable solvent such 1,2-dichloroethane or chloroform. The reaction can be carried out at an elevated temperature such as 80° C. or the reflux temperature of the solvent. The product can be isolated by conventional methods. Some imidates of formula Hal-$(CH_2)_d$—$CH_2$—C(=NH)—O-alkyl are known; others can be prepared by known methods. Ethyl chloroacetimidate hydrochloride, which can be used to provide a compound of Formula XXIII in which d is 0, is a known compound that can be prepared according to the literature procedure: Stillings, M. R. et al., *J. Med. Chem.*, 29, pp. 2280-2284 (1986).

When the carboxylic acid equivalent is an acid halide of formula Hal-$(CH_2)_d$—$CH_2$—C(O)Cl or Hal-$(CH_2)_d$—$CH_2$—C(O)Br, the reaction is conveniently carried out by adding the acid halide to a solution of a quinoline-3,4-diamine or [1,5]naphthyridine-3,4-diamine of Formula XXII in a suitable solvent such as dichloromethane or 1,2-dichloroethane in the presence of a tertiary amine such as triethylamine. The reaction can be carried out at ambient temperature or at a sub-ambient temperature. The product can be isolated by conventional methods.

The reaction with an acid halide of formula Hal-$CH_2$—$(CH_2)_d$—C(O)Cl or Hal-$CH_2$—$(CH_2)_d$—C(O)Br may be carried out in two parts, which include (i) adding the acid halide to a solution of a quinoline-3,4-diamine or [1,5]naphthyridine-3,4-diamine of Formula XXII in a suitable solvent such as dichloromethane or 1,2-dichloroethane optionally in the presence of a tertiary amine such as triethylamine to afford an amide intermediate and (ii) cyclizing to provide a 1H-imidazo[4,5-c]quinoline or 1H-imidazo[4,5-c][1,5]naphthyridine of Formula XXIII. The amide intermediate from part (i) can be optionally isolated using conventional techniques. The cyclization in part (ii) may be carried out by heating the amide intermediate from part (i) in a suitable solvent such as toluene. The cyclization in part (ii) can also be carried out in the presence of a base such as triethylamine.

In step (9) of Reaction Scheme I, the hydroxy protecting group on a 1H-imidazo[4,5-c]quinoline or 1H-imidazo[4,5-c][1,5]naphthyridine of Formula XXIII is removed to reveal the hydroxy group in a product of Formula XXIV. The deprotection reaction can be carried out using a variety of conventional methods, depending on the protecting group used. When P is a silyl group such as tert-butyldimethylsilyl, the deprotection can be carried out by heating the 1H-imidazo[4,5-c]quinoline or 1H-imidazo[4,5-c][1,5]naphthyridine of Formula XXIII with acetic acid in a suitable solvent such as water. The reaction may be carried out at 50° C., and the product can be isolated by conventional methods. Alternatively, tetrabutylammonium fluoride (TBAF) can be added to a solution of a 1H-imidazo[4,5-c]quinoline or 1H-imidazo[4,5-c][1,5]naphthyridine of Formula XXIII in a suitable solvent such as tetrahydrofuran (THF). The reaction can be carried out at a sub-ambient temperature, such as −78° C., and then warmed to ambient temperature, and the product can be isolated by conventional methods. When the reaction with TBAF is carried out in dichloromethane, a product of Formula XXV may be isolated, and the reaction shown in step (10) may be obviated.

In step (10) of Reaction Scheme I, a 1H-imidazo[4,5-c]quinoline or 1H-imidazo[4,5-c][1,5]naphthyridine of Formula XXIV is cyclized by an intramolecular displacement of the halogen under basic conditions. The reaction is conveniently carried out by adding a base such as potassium tert-butoxide to a solution of a compound of Formula XXIV in a suitable solvent such as THF. The reaction can be carried out at ambient temperature or at an elevated temperature. The product of Formula XXV can be isolated using conventional methods.

In step (11) of Reaction Scheme I, a 1H-imidazo[4,5-c]quinoline or 1H-imidazo[4,5-c][1,5]naphthyridine of Formula XXV is oxidized to provide a 1H-imidazo[4,5-c]quinoline-5N-oxide or 1H-imidazo[4,5-c][1,5]naphthyridine-5N-oxide of Formula XXVI using a conventional oxidizing agent capable of forming N-oxides. The reaction is conveniently carried out by adding 3-chloroperoxybenzoic acid to a solution of a compound of Formula XXV in a solvent such as chloroform or dichloromethane. The reaction can be carried out at ambient temperature. The product can be isolated using conventional methods.

In step (12) of Reaction Scheme I, a 1H-imidazo[4,5-c]quinoline-5N-oxide or 1H-imidazo[4,5-c][1,5]naphthyridine-5N-oxide of Formula XXVI is aminated to provide a 1H-imidazo[4,5-c]quinolin-6-amine or 1H-imidazo[4,5-c][1,5]naphthyridin-6-amine of Formula XXVII. Step (12) involves the activation of an N-oxide of Formula XXVI by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXVI in a suitable solvent such as dichloromethane or chloroform and then adding p-toluenesulfonyl chloride. The reaction can be carried out at ambient temperature, and the product or a pharmaceutically acceptable salt thereof can be isolated from the reaction mixture using conventional methods.

Alternatively, the oxidation and amination can be carried out as a one-pot procedure without isolating the N-oxide of Formula XXVI by adding 3-chloroperoxybenzoic acid to a solution of a compound of Formula XXV in a solvent such as dichloromethane or chloroform and then adding ammonium hydroxide and p-toluenesulfonyl chloride. The product of Formula XXVII or a pharmaceutically acceptable salt thereof can be isolated by conventional methods.

In step (13) of Reaction Scheme I, the benzyl group of a benzyloxy-1H-imidazo[4,5-c]quinoline or benzyloxy-1H-imidazo[4,5-c][1,5]naphthyridine of Formula XXVII is cleaved to provide a 1H-imidazo[4,5-c]quinolinol or 1H-imidazo[4,5-c][1,5]naphthyridinol of Formula XXVIII. The cleavage is conveniently carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula XXVII in a suitable solvent such as ethanol in the presence of a catalyst such as palladium on carbon. The reaction is carried out at an elevated temperature, for example, the reflux temperature of the solvent. The product or a pharmaceutically acceptable salt thereof can be isolated using conventional methods.

In step (14) of Reaction Scheme I a 1H-imidazo[4,5-c]quinolinol or 1H-imidazo[4,5-c][1,5]naphthyridinol of Formula XXVIII is converted to an ether-substituted 1H-imidazo[4,5-c]quinoline or 1H-imidazo[4,5-c][1,5]naphthyridine of Formula XXIX, a subgenus of Formula I, using a Williamson-type ether synthesis. The reaction is effected by treating a compound of Formula XXVIII with an alkyl halide of Formula Halide-$R_{3-1}$ in the presence of a base. The reaction is conveniently carried out by combining the alkyl halide with a compound of Formula XXVIII in a solvent such as DMF in the presence of a suitable base such as cesium carbonate. The reaction can be carried out at ambient temperature or at an elevated temperature, for example 65° C. or 85° C. Optionally, tetrabutylammonium bromide can be added. Alternatively, the reaction can be carried out by treating a solution of a compound of Formula XXVIII in a solvent such as DMF with sodium hydride and then adding a reagent of formula Halide-$R_{3-1}$. The product or a pharmaceutically acceptable salt thereof can be isolated using conventional methods.

Numerous reagents of formulas Halide—Z—Y—$F_4$, Halide—Z-Het, and Halide—Z-HetAr, wherein Z, Y, R, Het, and HetAr are as defined above, are commercially available. These include, for example, bromo-substituted ketones such as 2-bromoacetophenone, bromo-substituted esters such as ethyl bromoacetate, heterocycles such as 2-(bromomethyl)tetrahydro-2H-pyran, 4-(2-chloroethyl)morpholine hydrochloride, 1-(2-chloroethyl)pyrrolidine hydrochloride, and 1-(2-chloroethyl)piperidine hydrochloride, and heteroarylalkylenyl halides such as 4-(chloromethyl)thiazole hydrochloride, 2-chloromethyl-1-methyl-1H-imidazole hydrochloride, and 3-(bromomethyl)-5-methylisoxazole. Other reagents of Formulas Halide—Z—Y—$R_4$, Halide—Z—$R_5$, Halide—Z—Y—X—Y—$R_4$, and Halide—Z-Het, wherein Z, Y, X, $R_4$, $R_5$, and Het are as defined above, can be prepared using conventional synthetic methods; for example, a bromo-substituted acid halide of formula ClC(O)—Z—Br or BrC(O)—Z—Br can be treated with a secondary amine in a suitable solvent such as dichloromethane to provide a variety of bromo-substituted amides of formula Br—Z—C(O)—N($R_8$)—$R_4$,

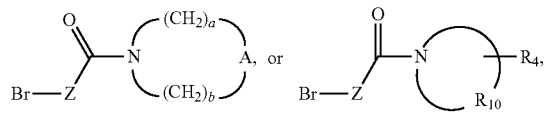

wherein $R_8$, $R_{10}$, A, a, and b are as defined above. The reaction can be run at a sub-ambient temperature such as −25° C., and the product can be isolated using conventional methods. Also, the preparation of compounds of formula I—Z—N($R_8$)-Boc, wherein Boc is tert-butoxycarbonyl, has been reported (U.S. Pat. No. 6,660,747).

Step (14) of Reaction Scheme I can alternatively be carried out by treating a compound of Formula XXVIII with an alcohol of Formula HO—$R_{3-1}$ under Mitsunobu reaction conditions. Numerous alcohols of formulas HO—Z—Y—$R_4$, HO—Z—$R_5$, HO—Z-Het, and HO—Z-HetAr are commercially available; for example, 1-(3-hydroxypropyl)pyrrolidin-2-one, 1-(2-hydroxyethyl)pyrrolidin-2-one, tert-butyl 4-hydroxypiperidine-1-carboxylate, and 3-pyridylcarbinol. Other alcohols of formula HO—$R_{3-1}$ can be prepared using conventional synthetic methods. The reaction is conveniently carried out by out by adding triphenylphosphine and an alcohol of Formula HO—$R_{3-1}$ to a solution of a compound of Formula XXVIII in a suitable solvent such as tetrahydrofuran and then slowly adding diisopropyl azodicarboxylate or diethyl azodicarboxylate. The reaction can be carried out at ambient temperature or at a sub-ambient temperature, such as 0° C. The product or a pharmaceutically acceptable salt thereof can be isolated using conventional methods.

Compounds prepared in step (14) can undergo further synthetic elaboration. For example, in a compound of Formula XXIX wherein —$R_{3-1}$ is —Z—N($R_8$)-Boc, prepared as described above, the Boc protecting group can be removed to provide an amino-substituted compound wherein —$R_{3-1}$ is —Z—N($R_8$)H. The reaction is conveniently carried out by adding a solution of hydrochloric acid in ethanol to a Boc protected amine; the reaction can be carried out at room temperature or an elevated temperature, for example, the reflux temperature of the solvent. The product or a pharmaceutically acceptable salt thereof can be isolated by conventional methods.

A compound of Formula XXIX wherein —$R_{3\text{-}1}$ is —Z—N($R_8$)H can be converted to a compound of Formula XXIX wherein —$R_{3\text{-}1}$ is —Z—N($R_8$)-Q-$R_4$ using conventional methods. For example, a compound of Formula XXIX wherein —$R_{3\text{-}1}$ is —Z—N($R_8$)H can react with an acid chloride of Formula $R_4$C(O)Cl to provide a compound of Formula XXIX in which —$R_{3\text{-}1}$ is —Z—N($R_8$)—C(O)—$R_4$. In addition, a compound of Formula XXIX wherein —$R_{3\text{-}1}$ is —Z—N($R_8$)H can react with sulfonyl chloride of Formula $R_4$S(O)$_2$Cl or a sulfonic anhydride of Formula ($R_4$S(O)$_2$)$_2$O to provide a compound of Formula XXIX in which —$R_{3\text{-}1}$ is —Z—N($R_8$)—S(O)$_2$—$R_4$. Numerous acid chlorides of Formula $R_4$C(O)Cl, sulfonyl chlorides of Formula $R_4$S(O)$_2$Cl, and sulfonic anhydrides of Formula ($R_4$S(O)$_2$)$_2$O are commercially available; others can be readily prepared using known synthetic methods. The reaction is conveniently carried out by adding the acid chloride of Formula $R_4$C(O)Cl, sulfonyl chloride of Formula $R_4$S(O)$_2$Cl, or sulfonic anhydride of Formula ($R_4$S(O)$_2$)$_2$O to a solution of a compound of Formula XXIX wherein —$R_{3\text{-}1}$ is —Z—N($R_8$)H in a suitable solvent such as chloroform, dichloromethane, or 1-methyl-2-pyrrolidinone. Optionally a base such as triethylamine, pyridine, or N,N-diisopropylethylamine, or a combination thereof can be added. The reaction can be carried out at room temperature or initially at a sub-ambient temperature such as 0° C. and then warming to room temperature. The product or pharmaceutically acceptable salt thereof can be isolated using conventional methods.

Compounds of Formula XXIX where —$R_{3\text{-}1}$ is —Z—$R_5$ and $R_5$ is

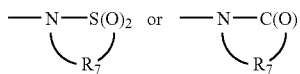

can be prepared by treating a compound of Formula XXIX wherein —$R_{3\text{-}1}$ is —Z—NH$_2$ with a chloroalkanesulfonyl chloride of Formula C$_1$—$R_7$S(O)$_2$Cl or a chloroalkanoyl chloride of Formula Cl—$R_7$C(O)Cl. The reaction is conveniently carried out by adding the chloroalkanesulfonyl chloride or chloroalkanoyl chloride to a solution of the aminoalkyl-substituted compound of Formula XXIX in a suitable solvent such as chloroform at ambient temperature. The insoluble intermediate chloroalkanesulfonamide or chloroalkanamide can then be treated with a base such as 1,8-diazabicyclo[5.4.0]undec-7-ene in a suitable solvent such as DMF to effect the cyclization. The product or a pharmaceutically acceptable salt thereof can be isolated using conventional methods.

Ureas of Formula XXIX, wherein —$R_{3\text{-}1}$ is —Z—N($R_8$)-Q-$R_4$, Q is —C($R_6$)—NH—W—, $R_6$ is =O, and W is a bond, can be prepared by reacting a compound of Formula X=X wherein —$R_{3\text{-}1}$ is —Z—N($R_8$)H with isocyanates of Formula $R_4$N=C=O. Numerous isocyanates of Formula $R_4$N=C=O are commercially available; others can be readily prepared using known synthetic methods. The reaction can be conveniently carried out by adding the isocyanate of Formula $R_4$N=C=O to a solution of the compound of Formula XXIX wherein —$R_{3\text{-}1}$ is —Z—N($R_8$)H in a suitable solvent such as dichloromethane or chloroform. Optionally a base such as triethylamine can be added. The reaction can be carried out at room temperature or initially at a sub-ambient temperature such as 0° C. and warming to room temperature. Alternatively, an aminoalkyl-substituted compound of Formula XXIX can be treated with an isocyanate of Formula $R_4$(CO)N=C=O, a thioisocyanate of Formula $R_4$N=C=S, a sulfonyl isocyanate of Formula $R_4$S(O)$_2$N=C=O, or a carbamoyl chloride of Formula $R_4$N—($R_8$)—C(O)Cl,

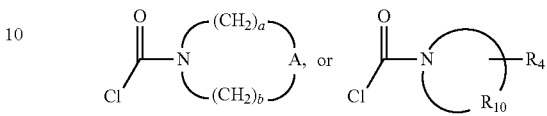

to provide a compound of Formula XXIX, where $R_{3\text{-}1}$ is —Z—N($R_8$)-Q-$R_4$,

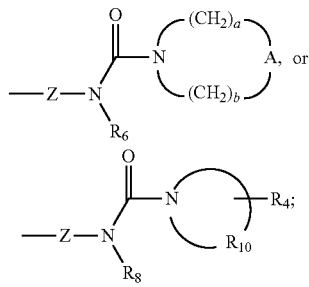

wherein Q is —C($R_6$)—N($R_8$)—W—, where $R_6$, $R_8$, and W are defined as above. The product or a pharmaceutically acceptable salt thereof can be isolated using conventional methods.

Sulfamides of Formula XXIX, where —$R_{3\text{-}1}$ is —Z—N($R_8$)—S(O)$_2$—N($R_8$)—$R_4$ can be prepared by reacting a compound of Formula XXIX wherein —$R_{3\text{-}1}$ is —Z—N($R_B$)H with sulfuryl chloride to generate a sulfamoyl chloride in situ, and then reacting the sulfamoyl chloride with an amine of formula HN($R_8$)$R_4$. Alternatively, sulfamides of Formula XXIX can be prepared by reacting a compound of Formula XXIX wherein —$R_{3\text{-}1}$ is —Z—N($R_8$)H with a sulfamoyl chloride of formula $R_4$($R_8$)N—S(O)$_2$Cl. The product or a pharmaceutically acceptable salt thereof can be isolated using conventional methods. Many amines of Formula HN($R_9$)$R_4$ and some sulfamoyl chlorides of formula $R_4$($R_9$)N—S(O)$_2$Cl are commercially available; others can be prepared using known synthetic methods. The product or a pharmaceutically acceptable salt thereof can be isolated using conventional methods.

Compounds of Formula XXIX, wherein —$R_{3\text{-}1}$ is —Z—N($R_8$)—$R_4$ can be prepared by reductive alkylation of a compound of Formula XXIX wherein —$R_{3\text{-}1}$ is —Z—N($R_9$)H, wherein $R_8$ is hydrogen. The alkylation is conveniently carried out in two parts by (i) adding an aldehyde or ketone to a solution of the aminoalkyl-substituted compound of Formula XXIX or a salt thereof in a suitable solvent such as DMF in the presence of a base such as N,N-diisopropylethylamine. In part (ii) the reduction is carried out by adding a suitable reducing agent such as the borane-pyridine complex. Both part (i) and part (ii) can be carried out at ambient temperature, and the product or a pharmaceutically acceptable salt thereof can be isolated using conventional methods. The reductive alkylation can be followed by reaction with an acid chloride, sulfonyl chloride, sulfonic anhydride, isocyanate, or carbamoyl chloride as described above to provide a compound of Formula XXIX, wherein $R_{3-1}$ is —Z—N($R_8$)-Q-$R_4$, wherein Z, $R_4$, $R_8$, and Q are as defined above.

A compound of Formula XXIX wherein —$R_{3-1}$ is

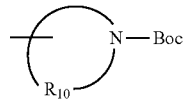

prepared by methods described above, can be converted to a compound of Formula XXIX wherein —$R_{3-1}$ is

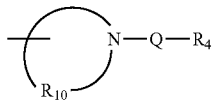

using the chemistry described above for compounds wherein —$R_{3-1}$ is —Z—N($R_8$)-Boc.

Isomers of the compound of Formula LV or Formula XVII, wherein E is nitrogen and on a different position of the pyridine ring, can also be synthesized and can be used to prepare compounds of the invention according to the methods of Reaction Scheme I.

Reaction Scheme I

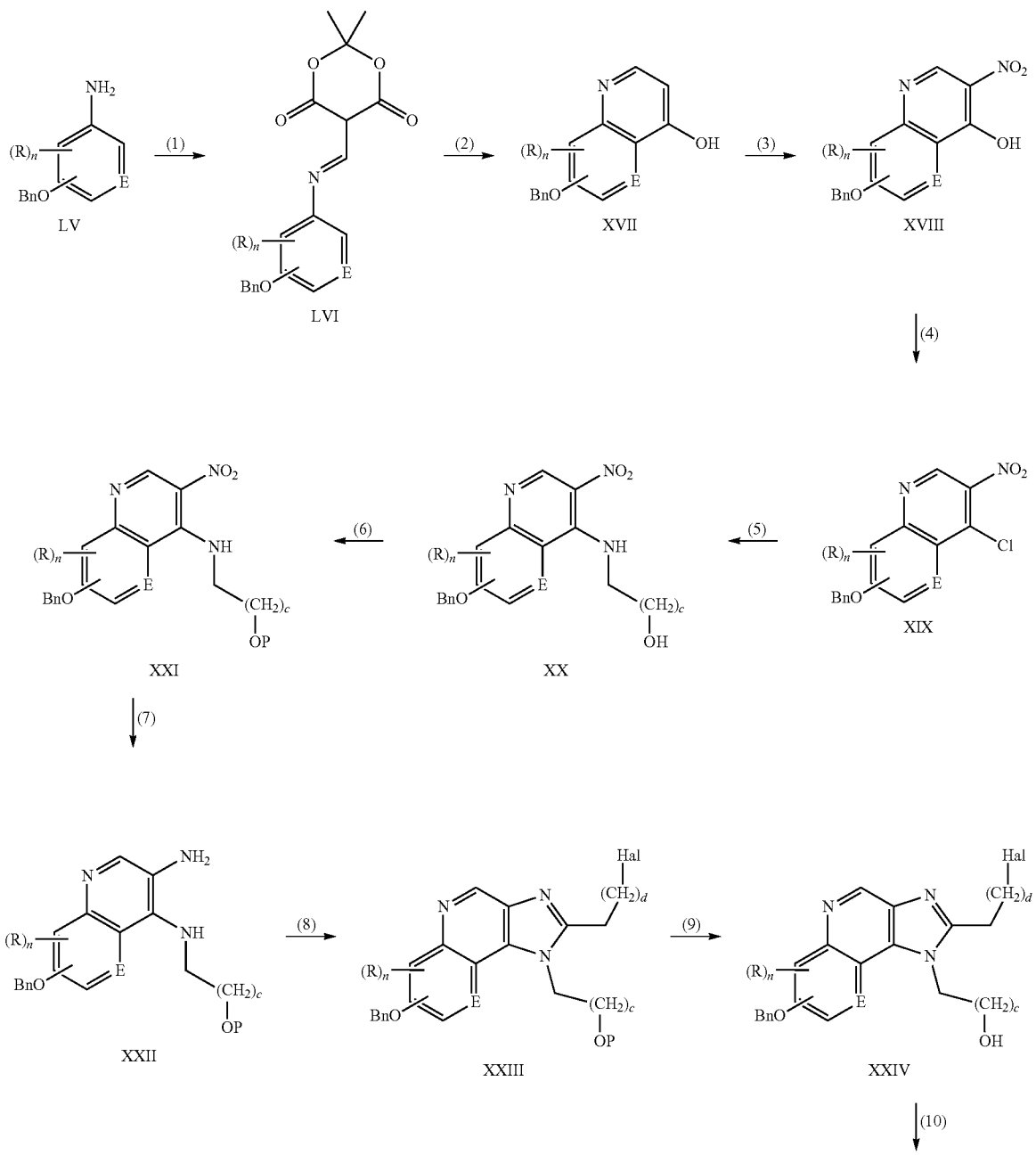

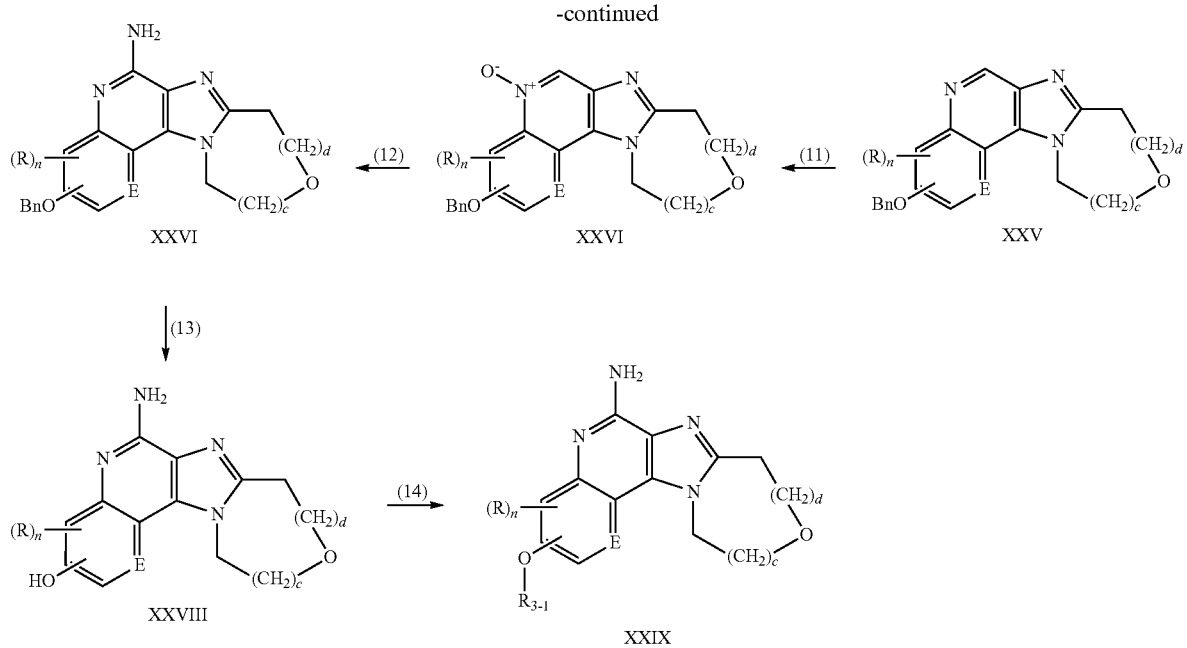

Compounds of the invention can also be prepared according to Reaction Scheme II, wherein E, R, c, d, and n are as defined above; $Z_a$ is selected from the group consisting of alkylene, alkenylene, and alkynylene wherein alkylene, alkenylene, and alkynylene can be optionally interrupted with one or more —O— groups; and $R_{3-2}$ is —Z-Het, —Z-Het'-$R_4$, or —Z-Het'-Y—$R_4$, wherein Het or Het' is attached to Z at a nitrogen atom.

In step (1) of Reaction Scheme II, a 1H-imidazo[4,5-c]quinolinol or 1H-imidazo[4,5-c][1,5]naphthyridinol of Formula XXVIII is treated with a dihalide of Formula I—Z—Cl or Br—Z—Cl using the Williamson conditions described in step (14) of Reaction Scheme I to provide a chloro-substituted compound of Formula XXX. The product or a pharmaceutically acceptable salt thereof can be isolated using conventional methods.

In step (2) of Reaction Scheme II, a chloro-substituted compound of Formula XXX is treated with a cyclic secondary amine to provide a compound of Formula XXXI, a subgenus of Formula I. Many cyclic secondary amines are commercially available, such as unsubstituted or substituted pyrrolidines, piperidines, morpholines, and piperazines; others can be prepared using conventional methods. The reaction is conveniently carried out by adding a cyclic secondary amine to a compound of Formula XXX in a suitable solvent such as DMF. The reaction is conveniently carried out in the presence of a base such as potassium carbonate at an elevated temperature such as 65° C. The product of Formula XXXI or a pharmaceutically acceptable salt thereof can be isolated by conventional methods.

A compound of Formula XXX is also a useful starting material to provide a number of other compounds of the invention. For example, a compound of Formula XXX can be treated with a non-cyclic secondary amine or a mercaptan under the conditions described in step (2) above to provide a compound in which $R_{3-2}$ is —Z—Y—$R_4$, wherein $R_4$ is as defined above and Y is —N($R_8$)-Q- or —S—, wherein Q is a bond and $R_8$ is as defined above. In another example, a compound of Formula XXX can be treated under the same conditions with a substituted phenol to provide a compound wherein $R_{3-2}$ is —Z—Y—X—Y—$R_4$, in which the Y bonded to Z is —O—, X is phenylene, and $R_4$ and the Y bonded to $R_4$ are as defined above.

Reaction Scheme II

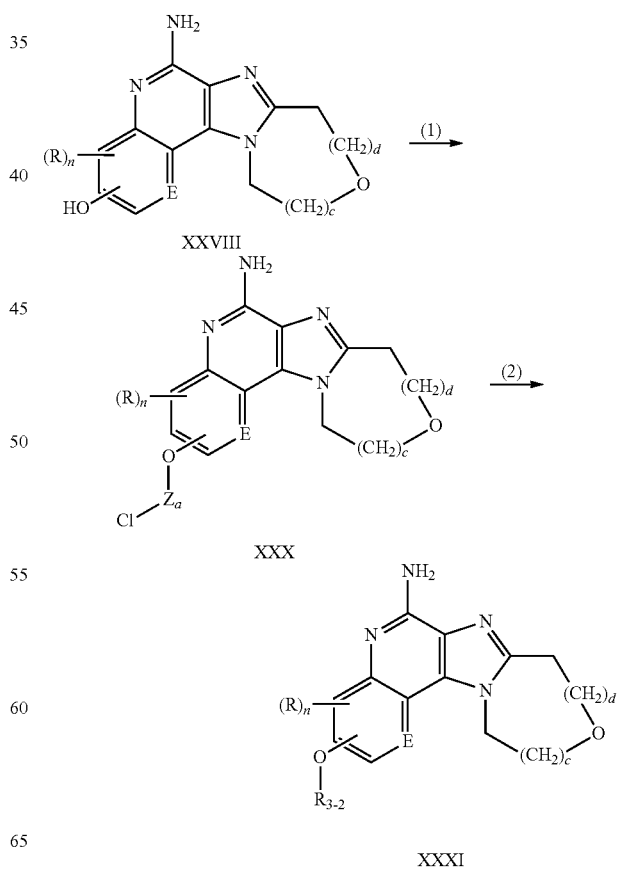

Compounds of the invention can be prepared according to Reaction Scheme III, wherein E, R, c, d, and n are as defined above; hal is —Br or —I; $R_{3-3}$ is selected from the group consisting of —C(H)=C(H)—$Z_b$—Y—$R_4$, —C(H)=C(H)—$Z_b$—Y—X—Y—$R_4$, —C(H)=C(H)—$Z_b$-$R_5$, —C(H)=C(H)—$Z_b$-Het, —C(H)=C(H)—$Z_b$-Het'-$R_4$, —C(H)=C(H)—$Z_b$-Het'-Y—$R_4$, —N($R_8$)—C($R_6$)—$R_4$, —N($R_8$)—SO$_2$—$R_4$, and

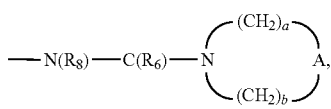

wherein $R_8$, $R_6$, $R_5$, $R_4$, Y, Het, Het', and X, are as defined above, and $Z_b$ is selected from the group consisting of a bond and alkylene wherein alkylene can be optionally interrupted with one or more —O— groups; and $R_{34}$ is selected from the group consisting of —CH$_2$—CH$_2$—$Z_b$—Y—$R_4$, —CH$_2$—CH$_2$—$Z_b$—Y—X—Y—$R_4$, —CH$_2$—CH$_2$—$Z_b$-$R_5$, —CH$_2$—CH$_2$—$Z_b$-Het, —CH$_2$—CH$_2$—$Z_b$-Het'-$R_4$, and —CH$_2$—CH$_2$—$Z_b$-Het'-Y—$R_4$, wherein $R_5$, $R_4$, $Z_b$, Y, X, Het, and Het' are as defined above. It is understood by one skilled in the art that certain substrates are not compatible with the Heck reaction chemistry described in step (13) of Reaction Scheme III; see, R. F. Heck, in *Comprehensive Organic Synthesis*, Vol. 4 (Eds.: B. M. Trost, I. Fleming), Pergamon Press, Oxford, p. 833, (1991). For example, it is understood by one skilled in the art that $Z_b$ is other than a bond when a Y group bonded to $Z_b$ is —O—, —O—C($R_6$)—, —OC(O)—O—, —O—C($R_6$)—N($R_8$)—,

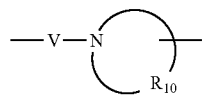

wherein V is —O—C($R_6$)—, or

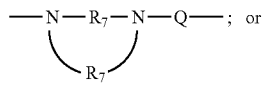

when then the $R_5$ bonded to $Z_b$ is

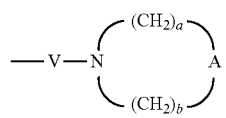

wherein V is —O—C($R_6$)—; or when $Z_b$ is attached to a nitrogen atom in Het or Het'.

Steps (1) through (12) of Reaction Scheme III are analogous to steps (1) through (12) of Reaction Scheme I with hal used as a substituent instead of the benzyloxy group. Alternatively, trifluoromethanesulfonate-substituted compounds, wherein hal in a compound of Formula XXXIII is replaced with —OSO$_2$CF$_3$ can be used. Trifluoromethanesulfonate-substituted compounds can readily be prepared from compounds of Formula XXVIII using conventional methods.

The Heck reaction is used in step (13) of Reaction Scheme III to provide compounds of Formula XIV, wherein $R_{3-3}$ is selected from the group consisting of —C(H)=C(H)—$Z_b$—Y—$R_4$, —C(H)=C(H)—$Z_b$—Y—X—Y—$R_4$, —C(H)=C(H)—$Z_b$-$R_5$, —C(H)=C(H)—$Z_b$-Het, —C(H)=C(H)—$Z_b$-Het'-$R_4$, —C(H)=C(H)—$Z_b$-Het'-Y—$R_4$. The Heck reaction is carried out by coupling a compound of Formula XXXIII with a compound of the Formula H$_2$C=C(H)—$Z_b$—Y—$R_4$, H$_2$C=C(H)—$Z_b$—Y—X—Y—$R_4$, H$_2$C=C(H)—$Z_b$-$R_5$, H$_2$C=C(H)—$Z_b$-Het, H$_2$C=C(H)—$Z_b$-Het'-$R_4$, or H$_2$C=C(H)—$Z_b$-Het'-Y—$R_4$. Several of these vinyl-substituted compounds are commercially available; others can be prepared by known methods. For example, vinyl-substituted compounds are readily prepared from aldehydes, primary alcohols, or primary alkyl halides using a variety of conventional methods. The Heck reaction is conveniently carried out by combining the compound of Formula XXXIII and the vinyl-substituted compound in the presence of palladium (II) acetate, triphenylphosphine or tri-ortho-tolylphosphine, and a base such as triethylamine or cesium carbonate in a suitable solvent such as acetonitrile, toluene, or N,N-dimethylformamide DMF). The reaction can be carried out at an elevated temperature such as 85° C. to 125° C. under an inert atmosphere. The product of Formula XIV, a subgenus of Formulas I, or a pharmaceutically acceptable salt thereof can be isolated using conventional methods.

A copper-mediated coupling reaction can be used to prepare compounds of Formula XXXIV, wherein $R_{3-3}$ is —N($R_8$)—C($R_6$)—$R_4$, —N($R_8$)—SO$_2$—$R_4$, or

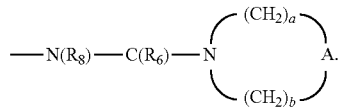

The reaction is conveniently carried out by combining the 1H-imidazo[4,5-c]quinolin-4-amine or 1H-imidazo[4,5-c][1,5]naphthyridin-4-amine of the Formula XXXIII and an amide, sulfonamide, or urea of formula HN($R_8$)—C($R_6$)—$R_4$, HN($R_8$)—SO$_2$—$R_4$, or

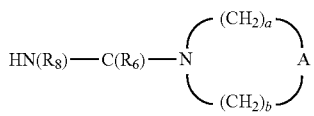

in the presence of copper (I) iodide, potassium phosphate, and racemic trans-1,2-diaminocyclohexane in a suitable solvent such as 1,4-dioxane. The reaction can be carried out at an elevated temperature such as 110° C. Many amides, sulfonamides, and ureas of these formulas are commercially available; others can be made by conventional methods. The compound or a pharmaceutically acceptable salt thereof can be isolated using conventional methods. These reaction conditions can also be used to couple a compound of Formula XIII with a wide variety of nitrogen-containing heterocycles to provide a compound of Formula XXXIV wherein $R_{3-3}$ is -Het, -Het'-$R_4$, or -Het'Y—$R_4$, wherein Het or Het' is attached to the quinoline or naphthyridine ring through a nitrogen atom. In addition, certain of these compounds of Formula XXXIV wherein $R_{3-3}$ is -Het, -Het'-$R_4$, or -Het'Y—$R_4$, wherein Het or Het' is attached to the quinoline or naphthyridine ring through a nitrogen atom, can be prepared using a palladium-mediated coupling, which is conveniently carried out by combining the 1H-imidazo compound of the Formula XXIII and the nitrogen-containing heterocyclyl compound in the presence of tris(dibenzylideneacetone)dipalladium, (±)-2,2'-bis(diphenylphosphino)-1,1'-binaphthyl, sodium tert-butoxide, and a suitable solvent such as toluene. The reaction can be carried out at an elevated temperature such as 80° C. The compound or a pharmaceutically acceptable salt thereof can be isolated using conventional methods.

The compounds of Formula XXXIV prepared by the Heck reaction, can undergo reduction of the alkenylene group present to provide compounds of Formula XXXV. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product of Formula XXXV, a subgenus of Formula I, or a pharmaceutically acceptable salt thereof can be isolated using conventional methods.

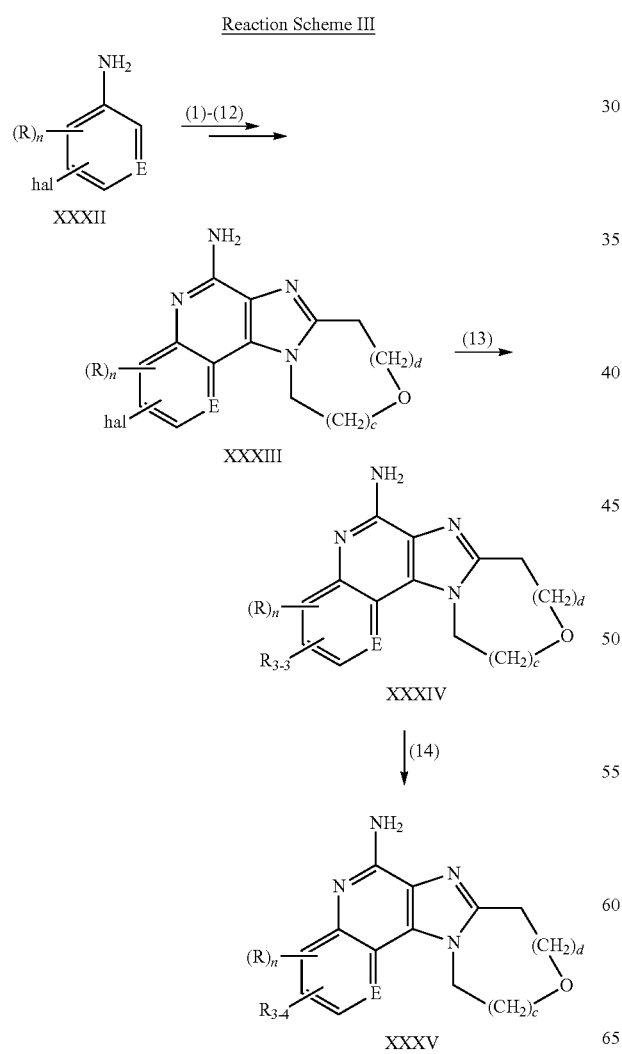

Reaction Scheme III

For some embodiments, compounds of the invention are prepared according to Reaction Scheme IV, wherein E, $R_4$, $R_8$, A, R, $Z_b$, hal, a, b, c, d, and n are as defined above. In step (1) of Reaction Scheme 1V, a compound of Formula XXXIII is coupled with an ester of formula $H_2C$=C(H)—C(O)—Oalkyl to provide an ester-substituted 1H-imidazo[4,5-c]quinolin-4-amine or 1H-imidazo[4,5-c][1,5]naphthyridin-4-amine of Formula XXXVI, a subgenus of Formula I. The reaction can be carried out under the Heck reaction conditions described in step (13) of Reaction Scheme III, and the product can be isolated by conventional methods. Some esters of formula $H_2C$=C(H)—C(O)—Oalkyl, for example methyl acrylate and methyl methacrylate, are commercially available; others can be prepared by known methods. The conditions described in step (14) of Reaction Scheme III may then be used to reduce the double bond in a compound of Formula XXXVI in step (2) of Reaction Scheme IV to provide an ester-substituted 1H-imidazo[4,5-c]quinolin-4-amine or 1H-imidazo[4,5-c][1,5]naphthyridin-4-amine of Formula XXXVII, a subgenus of Formula I.

In step (3) of Reaction Scheme IV, the ester group of a 1H-imidazo[4,5-c]quinolin-4-amine or 1H-imidazo[4,5-c][1,5]naphthyridin-4-amine of Formula XXXVII undergoes base-promoted hydrolysis to the carboxylic acid of Formula XXXVIII. The hydrolysis reaction is conveniently carried out by combining a compound of Formula XXXVII with a base such as potassium hydroxide or sodium hydroxide in a suitable solvent mixture such as an alcohol/water mixture, preferably a methanol/water mixture. The reaction can be carried out at room temperature, and the product of Formula XXXVIII, a subgenus of Formula I, or a pharmaceutically acceptable salt thereof can be isolated by conventional methods.

A carboxylic acid of Formula XXVIII is converted into an amide of Formula XXXIX or XL in step (4) or (4a) of Reaction Scheme IV using conventional methods. The reaction is conveniently carried out by treating a solution of a carboxylic acid of Formula XXXVIII with a secondary amine of formula $HN(R_8)R_4$ or

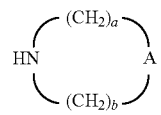

and a coupling agent, such as 1-[3-(dimethylamino)propyl-3-ethylcarbodiimide hydrochloride, in the presence of 1-hydroxybenzotriazole. The reaction can be carried out at room temperature in a suitable solvent such as DMF, and the product of Formula X or XL, which are subgenera of Formula I, or a pharmaceutically acceptable salt thereof, can be isolated by conventional methods. Numerous secondary amines are commercially available; others can be prepared by known synthetic methods.

Reaction Scheme IV

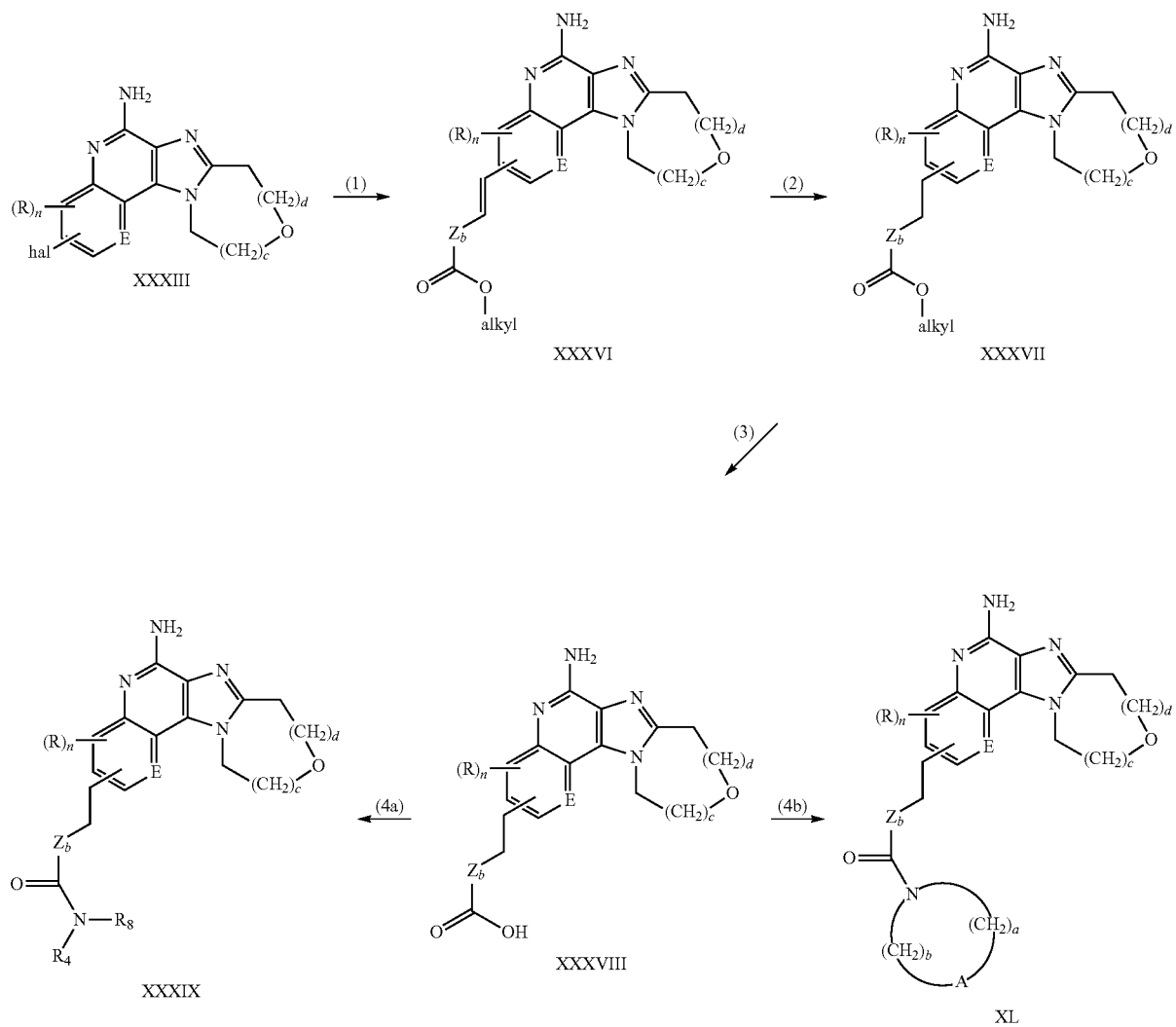

Compounds of the invention can also be prepared according to Reaction Scheme V, wherein Bn, E, R, $R_{3-1}$, and n are as defined above; P is an amino protecting group; and $D_a$ is —$(CH_2)_{1-4}$—. In step (1) of Reaction Scheme V, a benzyloxy-4-chloro-3-nitroquinoline or benzyloxy-4-chloro-3-nitro[1,5]naphthyridine of Formula XLI is reacted with tert-butylamine in the presence of base, and the tert-butyl group is subsequently removed under acidic conditions to provide a 3-nitroquinolin-4-amine or 3-nitro[1,5]naphthyridin-4-amine of Formula XLII, which is reduced in step (2) to provide a quinoline-3,4-diamine or [1,5]naphthyridine-3,4-diamine of Formula XLIII. In step (3) of Reaction Scheme V, a quinoline-3,4-diamine or [1,5]naphthyridine-3,4-diamine of Formula XLIII is reacted with acetic acid or acetyl chloride to provide a 2-methyl-1H-imidazo[4,5-c]quinoline or a 2-methyl-1H-imidazo[4,5-c][1,5]naphthyridine of Formula XLIV, which undergoes protection at the 1-position in step (4) with a suitable protecting group. In step (5) of Reaction Scheme V, the 2-methyl group of a 1H-imidazo[4,5-c]quinoline or 1H-imidazo[4,5-c][1,5]naphthyridine of Formula XLV is deprotonated with n-butyllithium and subsequently reacted with an alkylating agent of formula Br—$CH_2$-$D_a$-$CH_2$—Cl, and the product of Formula XLVI is then deprotected using conventional methods to provide a 1H-imidazo[4,5-c]quinoline or 1H-imidazo[4,5-c][1,5]naphthyridine of Formula XLVII. The compound of Formula XLVII is then cyclized to provide a compound of Formula XLVIII. Steps (1) through (7) of Reaction Scheme V can be carried out using the conditions described in U.S. Pat. No. 5,482,936 (Lindstrom).

Steps (8) through (11) of Reaction Scheme V are analogous to steps (11) through (14) of Reaction Scheme I and can be carried out using the same methods. The product of Formula LII, a subgenus of Formula I, or a pharmaceutically acceptable salt thereof can be isolated using conventional methods.

Reaction Scheme V

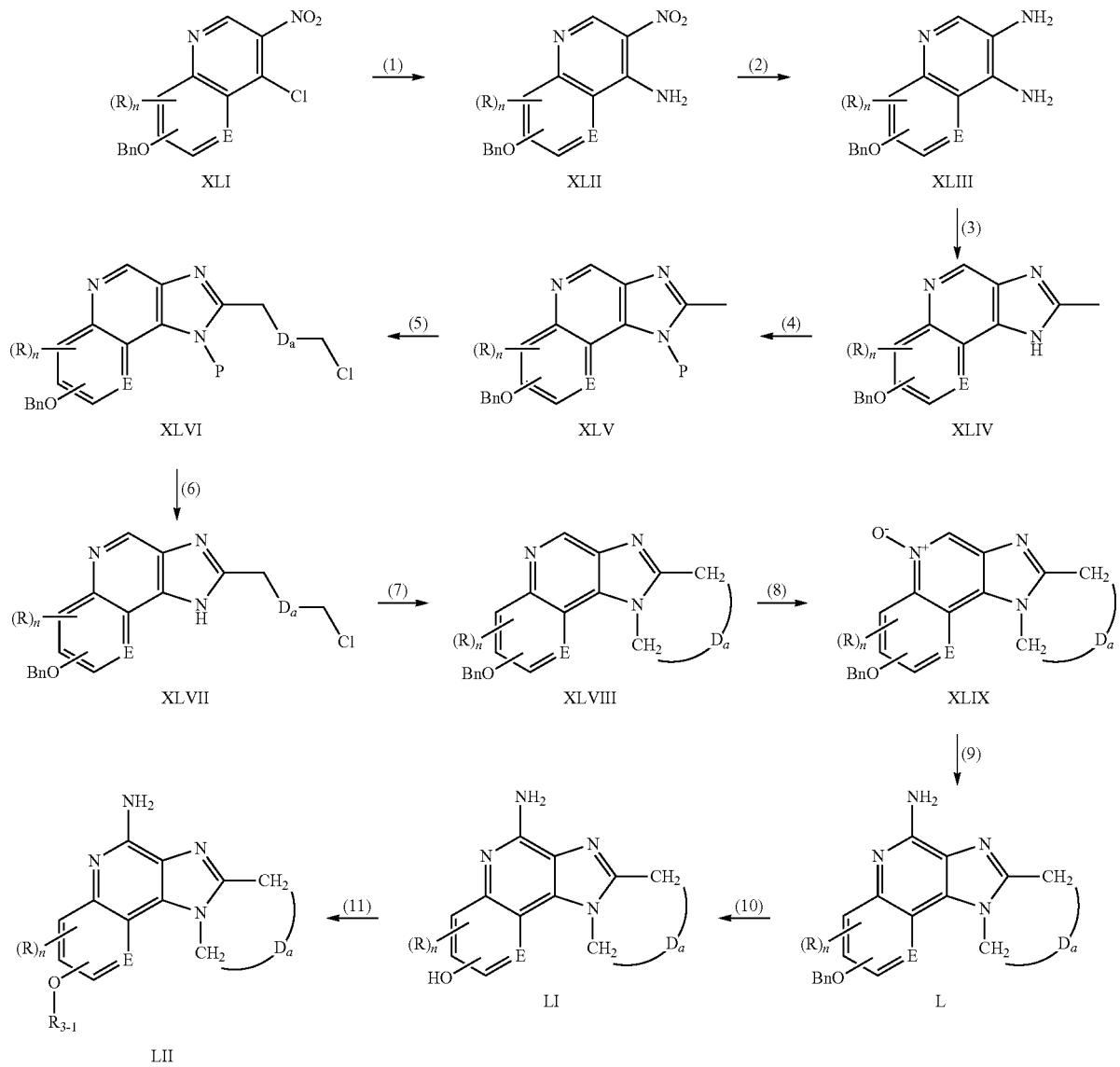

Compounds of the invention can also be prepared using variations of the synthetic routes shown in Reaction Schemes I through V that would be apparent to one of skill in the art. For example, the synthetic routes shown in Reaction Scheme II, III, and IV for the preparation of compounds wherein D is —($CH_2$)$_c$—O—($CH_2$)$_d$— can be used to prepare compounds wherein D is —($CH_2$)$_{1-4}$— using intermediates from Reaction Scheme V. In addition, the order of steps may be changed in Reaction Schemes I and V to prepare compounds of the invention. Also, the synthetic elaboration of amino-substituted compounds described in Reaction Scheme I can also be applied to Reaction Scheme III when a protected amino group, for example, a phthalimide-protected amino group, is introduced using the Heck reaction chemistry described in step (13) of Reaction Scheme III and then deprotected using conventional methods. Compounds of the invention can also be prepared using the synthetic routes described in the EXAMPLES below.

For certain embodiments, compounds of the invention can be prepared according to Reaction Scheme VI, wherein $R_A$, $R_B$, G, and D are as defined above. Compounds of Formula I can be prepared according to the methods described above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")—R', —C(—$NY_1$)—R', —CH(OH)—C(O)—$OY_1$, —CH(O$C_{1-4}$alkyl)$Y_0$, —$CH_2Y_2$, or —CH($CH_3$)$Y_2$; wherein R' and R" are each independently $C_{1-10}$ alkyl, $C_{3-7}$ cycloalkyl, phenyl, or benzyl, each of which may be unsubstituted or substituted by one or more substituents independently selected from the group consisting of halogen, hydroxy, nitro, cyano, carboxy, $C_{1-6}$alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$; with the proviso that R" may also be hydrogen; each α-aminoacyl group is independently selected from racemic, D, or L-amino acids; $Y_1$ is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_2$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. Particularly useful compounds of Formula XVI are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at room temperature.

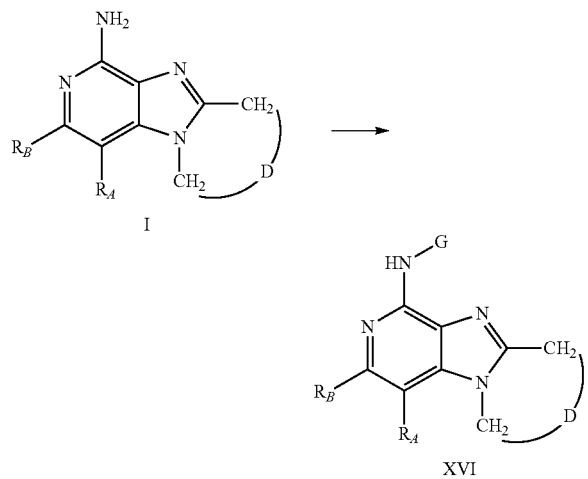

Reaction Scheme VI

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m² to about 5.0 mg/m², computed according to the Dubois method, in which the body surface area of a subject (m²) is computed using the subject's body weight: $m^2 = (wt\ kg^{0.425} \times height\ cm^{0.725}) \times 0.007184$, although in some embodiments the methods may be performed by administering a compound or salt or composition in a dose outside this range. In some of these embodiments, the method includes administering sufficient compound to provide a dose of from about 0.1 mg/m² to about 2.0 mg/m² to the subject, for example, a dose of from about 0.4 mg/m² to about 1.2 mg/m².

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytolidnes. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, or Bordetella;

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m² to about 5.0 mg/m², (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m² to about 2.0 mg/m² to the subject, for example, a dose of from about 0.4 mg/m² to about 1.2 mg/m².

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

3-(2-Morpholin-4-yl-2-oxoethoxy)-10,11-dihydro-8H-[1,4]oxazino[4',3':1,2]imidazo[4,5-c]quinolin-6-amine

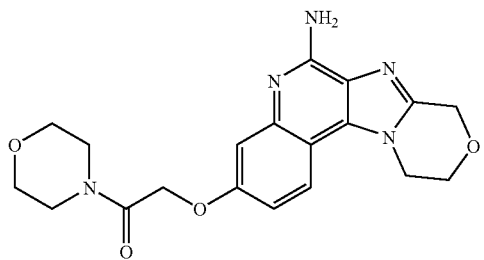

Part A

A mixture of triethyl orthoformate (92 milliliters (mL), 0.55 mole (mol)) and 2,2-dimethyl-[1,3]-dioxane-4,6-dione (75.3 grams (g), 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid.

¹H NMR (300 MHz, DMSO-d₆): δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A heat transfer fluid (800 mL) was heated to 100° C. and then slowly added to a flask containing DOWTHERM A heat transfer fluid (1.3 liters (L), heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder.

¹H NMR (300 MHz, DMSO-d₆): δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 molar (M)) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder.

¹H NMR (300 MHz, DMSO-d₆): δ12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H).

Part D

A 2-liter round bottom flask was charged with 7-(benzyloxy)-3-nitroquinolin-4-ol (100.0 g, 0.3 mol) and N,N-dimethylformamide (DMF) (650 mL). Phosphorous oxychloride (62.1 g, 37.7 mL, 1.2 equivalents (eq)) was slowly added dropwise. The resulting mixture was heated at 100° C. for 10 minutes, and then allowed to cool to 39° C. The reaction mixture was poured over ice (3 L). A brown precipitate formed. The mixture was diluted with water (1 L) and stirred to break up the precipitate. The precipitate was collected by vacuum filtration. The filter cake was washed with water (2 L) and air-dried on vacuum filter for 1 hour. The solid was dissolved in dichloromethane and placed in a separatory funnel. The water was removed, and the dichloromethane solution was dried over magnesium sulfate. The solution was then filtered through filter agent to provide a solution of 7-(benzyloxy)-4-chloro-3-nitroquinoline in dichloromethane (approximately 1700 mL).

Part E

A 3-liter 3-necked round bottom flask, equipped with addition funnel and overhead stirrer, was charged with the solution from Part D and triethylamine (94.2 mL, 2.0 eq). A solution of ethanolamine (21.1 mL, 0.35 mol, 1.04 eq) in dichloromethane (20 mL) was slowly added over 10 minutes. The reaction was stirred overnight at room temperature and then diluted with water (1 L). A precipitate was present and was isolated by filtration to provide 101.3 g of 2-{[7-(benzyloxy)-3-nitroquinolin-4-yl]amino}ethanol as a yellow solid.

Part F

A 2-necked 2-liter round bottom flask was charged with 2-{[7-(benzyloxy)-3-nitroquinolin-4-yl]amino}ethanol (95.0 g, 0.28 mol) and pyridine (400 mL). The suspension was heated to 65° C. To the resulting homogenous solution was added in one portion tert-butyldimethylsilyl chloride (46.4 g, 0.31 mol, 1.1 eq) and 4-(N,N-dimethylamino)pyridine (3.42 g, 0.028 mol, 0.1 eq). The reaction temperature rose to 87° C., was slowly cooled to 65° C., and was maintained overnight at this temperature. The reaction was determined to be incomplete. Additional tert-butyldimethylsilyl chloride (20 g, 0.13 mol, 0.5 eq) was added in one portion and the reaction temperature was increased to 70° C. for 8 hours. The reaction was still not complete. Additional tert-butyldimethylsilyl chloride (21.5 g, 0.14 mol, 0.5 eq) was added in one portion and the reaction was maintained at 70° C. overnight. The reaction was now complete. The reaction mixture was poured into a 2-liter flask, followed by an ethyl acetate rinse, and set aside over the weekend. A precipitate, determined to be pyridine hydrochloride, formed and was removed by filtration. The reaction mixture was then concentrated under reduced pressure to a brown/yellow solid. The solid was slurried in ethyl acetate and collected by filtration; this was repeated three times. The combined filtrates were washed with water and then concentrated to approximately one-third of the original volume until solid began to precipitate. The mixture was diluted with hexane (700 mL) and stirred for an additional hour. A light brown solid was collected by vacuum filtration and dried overnight to provide 102.6 g of 7-(benzyloxy)-N-(2-{[tert-butyl(dimethyl)silyl]oxy}ethyl)-3-nitroquinolin-4-amine, which was used without further purification in the next step.

Part G

A 3-liter stainless steel Parr vessel was charged sequentially with 5% platinum on carbon catalyst, acetonitrile (250 mL), 7-(benzyloxy)-N-(2-{[tert-butyl(dimethyl)silyl]oxy}ethyl)-3-nitroquinolin-4-amine (102 g, 0.225 mol), and additional acetonitrile (1250 mL). The vessel was evacuated and charged with hydrogen gas (30 psi, 2.1×10$^5$ Pa). The vessel was shaken overnight. The reaction mixture was then filtered through a layer of CELITE filter agent. The filter cake was rinsed with additional acetonitrile (2 L), and the combined filtrates were concentrated under reduced pressure to provide 95 g of 7-(benzyloxy)-N$^4$-(2-{[tert-butyl(dimethyl)silyl]oxy}ethyl)quinoline-3,4-diamine as an orange-green solid.

Part H

A 5-liter resin head reaction vessel, equipped with overhead stirrer, was charged under a nitrogen atmosphere with 7-(benzyloxy)-N$^4$-(2-{[tert-butyl(dimethyl)silyl]oxy}ethyl)quinoline-3,4-diamine (95 g, 0.225 mol) and 1,2-dichloroethane (2.25 L). To this solution was added in one portion ethyl chloroacetimidate hydrochloride (44.4 g, 0.28 mol, 1.25 eq). The reaction mixture was stirred vigorously overnight. At this time the reaction was not complete and the reaction mixture was heated at 65° C. for 6 hours. At this time the reaction was not complete and additional ethyl chloroacetimidate hydrochloride (8.8 g, 0.06 mol, 0.25 eq) was added. The reaction mixture was maintained at 65° C. overnight. The reaction was still not complete. Additional ethyl chloroacetimidate hydrochloride (9.5 g, 0.06 mol, 0.25 eq.) was added, and the reaction was maintained at 65° C. for an additional 6 hours. The reaction was now complete. The heat was removed and the reaction was left to slowly cool to room temperature overnight. The reaction mixture was filtered to remove a solid. The filtrate was washed sequentially with 5% sodium bicarbonate solution (800 mL), water (1 L) and brine (200 mL); dried over magnesium sulfate; filtered; and concentrated to 82 g of 7-(benzyloxy)-1-(2-{[tert-butyl(dimethyl)silyl]oxy}ethyl)-2-(chloromethyl)-1H-imidazo[4,5-c]quinoline as a dark viscous syrup that solidified upon standing.

Part I

A 500 mL round bottom flask was charged with 7-(benzyloxy)-1-(2-{[tert-butyl(dimethyl)silyl]oxy}ethyl)-2-(chloromethyl)-1H-imidazo[4,5-c]quinoline (30 g, 0.06 mol), acetic acid (300 mL), and water (60 mL). The suspension was heated at 50° C. for 24 hours. The heat was removed and the greenish homogeneous solution was concentrated to dryness. The solid was stirred in diethyl ether (300 mL) for 1 hour, isolated by vacuum filtration, washed with diethyl ether (100 mL), and dried on vacuum funnel to provide 23 g of 2-[7-(benzyloxy)-2-(chloromethyl)-1H-imidazo[4,5-c]quinolin-1-yl]ethanol as a green solid.

Part J

A 3-liter round bottom flask was charged with 2-[7-(benzyloxy)-2-(chloromethyl)-1H-imidazo[4,5-c]quinolin-1-yl]ethanol (23 g, 0.062 mol) and tetrahydrofuran (THF) (2 L). The resulting suspension was heated to 45° C. and a 1 M solution of potassium tert-butoxide in THF (120 mL, 0.12 mol, 1.9 eq) was slowly added. At this time the heat was removed and the reaction was quenched by the addition of saturated aqueous ammonium chloride solution (500 mL), and the resulting mixture was stirred for an additional hour. The organic layer was separated and concentrated to 16 g of 3-(benzyloxy)-10,11-dihydro-8H-[1,4]oxazino[4',3':1,2]imidazo[4,5-c]quinoline as a light yellow solid.

Part K

A 1-liter round bottom flask was charged with 3-(benzyloxy)-10,11-dihydro-8H-[1,4]oxazino[4',3':1,2]imidazo[4,5-c]quinoline (5.0 g, 15.1 millimoles (mmol)) and dichloromethane (200 mL). To this solution was slowly added in small portions 3-chloroperoxybenzoic acid (mCPBA) (5.2 g of 50% pure material, 15.1 mmol, 1.0 eq). The reaction was maintained at room temperature for 3 hours. Concentrated ammonium hydroxide (100 mL) was added followed by p-toluenesulfonyl chloride (3.2 g, 16.6 mmol, 1.1 eq) in small portions. The reaction was maintained at room temperature overnight. The reaction was quenched with water (200 mL) and stirred for an additional hour. The aqueous layer was separated and extracted with dichloromethane (3×50 mL). The combined organic fractions were concentrated to provide 3-(benzyloxy)-10,11-dihydro-8H-[1,4]oxazino[4',3':1,2]imidazo[4,5-c]quinolin-6-amine as an off-white solid. A small amount of product was recrystallized from acetonitrile and carried on to the next step.

Part L

A glass vial was charged with 3-(benzyloxy)-10,11-dihydro-8H-[1,4]oxazino[4',3':1,2]imidazo[4,5-c]quinolin-6- amine (0.1 g, 0.29 mmol) and a solution of 48% hydrogen bromide in acetic acid (4.0 mL). The mixture was heated at 100° C. overnight, cooled, and concentrated to provide 6-amino-10,11-dihydro-8H-[1,4]oxazino [4',3':1,2]imidazo [4,5-c]quinolin-3-ol as an off-white solid.

Part M

A solution of bromoacetyl bromide (3.0 mL, 0.034 mol) in dichloromethane (240 mL) was cooled to −25° C. A solution of morpholine (9.0 mL, 0.10 mol) in dichloromethane (20 mL) was slowly added over a period of one hour. After the addition was complete, the reaction was stirred at −25° C. for 15 minutes and then allowed to warm to ambient temperature. Dichloromethane was added, and the resulting solution was washed sequentially with water, 1N aqueous hydrogen chloride, and brine; dried over magnesium sulfate; filtered; and concentrated under reduced pressure to provide 4-(bromoacetyl)morpholine as a colorless oil.

Part N

A glass vial was charged with 4-(bromoacetyl)morpholine (0.05 g, 0.26 mmol, 1.1 eq), 6-amino-10,11-dihydro-8H-[1,4]oxazino[4',3':1,2]imidazo[4,5-c]quinolin-3-ol (0.06 g, 0.23 mmol), DMF (3 mL), and cesium carbonate (0.42 g, 1.3 mmol, 5 eq). The reaction mixture was heated at 90° C. overnight. The reaction was quenched with 30 mL water to provide an off-white precipitate. The solid was collected by vacuum filtration and recrystallized from acetonitrile to provide 0.011 g of 3-(2-morpholin-4-yl-2-oxoethoxy) 10,11-dihydro-8H-[1,4]oxazino[4',3':1,2]imidazo[4,5-c]quinolin-6-amine, mp 204-206° C.

Examples 2-43

A halide from the table below (1.1 equivalents) and anhydrous potassium carbonate (55 mg) were added to a test tube. For example 3, a few crystals of tetrabutylammonium bromide were also added. A solution of 6-amino-10,11-dihydro-8H-[1,4]oxazino[4',3':1,2]imidazo[4,5-c]quinolin-3-ol (26 mg, 0.1 mmol) in N,N-dimethylacetamide (1 mL) was added. The test tube was loosely capped and placed on a shaker at 60° C. overnight (approximately 18 hours) and then at 80° C. for 6 hours. The reaction mixture was filtered and then diluted with N,N-dimethylacetamide (200 μL). The solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the halide used for each example, the structure of the resulting compound, and the observed accurate mass for the isolated trifluoroacetate salt.

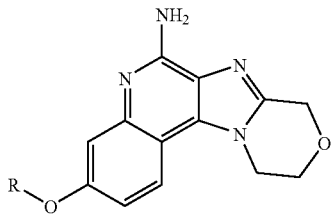

| Example | Reagent | R | Measured Mass (M + H) |
|---|---|---|---|
| 2 | None | H— | 257.1063 |
| 3 | 4-(Chloromethyl)thiazole | (thiazol-4-ylmethyl) | 354.1034 |
| 4 | 2-Bromoethyl methyl ether | H₃C—O—CH₂CH₂— | 315.1456 |
| 5 | 2-Bromopropanamide | (CH₃)CH(C(O)NH₂)— | 328.1426 |
| 6 | Methyl bromoacetate | H₃C—O—C(O)—CH₂— | 329.1238 |
| 7 | 5-Bromovaleronitrile | N≡C—(CH₂)₄— | 338.1599 |

-continued

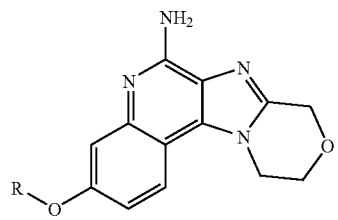

| Example | Reagent | R | Measured Mass (M + H) |
|---|---|---|---|
| 8 | Benzyl bromide | benzyl | 347.1486 |
| 9 | 2-Bromo-4-hydroxyvaleric acid gamma-lactone | 3,5-dimethyl-γ-butyrolactone | 355.1399 |
| 10 | (1-Bromoethyl)benzene | 1-phenylethyl | 361.1628 |
| 11 | alpha-Bromo-m-xylene | 3-methylbenzyl | 361.1641 |
| 12 | 1-(3-Bromopropyl)pyrrole | 3-(pyrrol-1-yl)propyl | 364.1790 |
| 13 | 2-Cyanobenzyl bromide | 2-cyanobenzyl | 372.1456 |
| 14 | 4-Cyanobenzyl bromide | 4-cyanobenzyl | 372.1472 |
| 15 | alpha-Bromo-m-tolunitrile | 3-cyanobenzyl | 372.1461 |
| 16 | 2-Bromoacetophenone | phenacyl | 375.1471 |

-continued

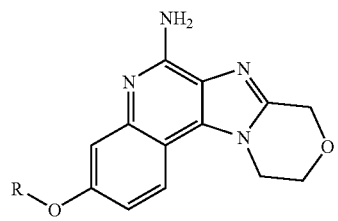

| Example | Reagent | R | Measured Mass (M + H) |
|---|---|---|---|
| 17 | 1-Bromo-3-phenylpropane | phenyl-propyl | 375.1814 |
| 18 | 3-Methoxybenzyl bromide | 3-methoxybenzyl | 377.1624 |
| 19 | beta-Bromophenetole | phenoxyethyl | 377.1597 |
| 20 | 2-Chlorobenzyl bromide | 2-chlorobenzyl | 381.1079 |
| 21 | 4-Chlorobenzyl bromide | 4-chlorobenzyl | 381.1099 |
| 22 | 2,4-Difluorobenzyl bromide | 2,4-difluorobenzyl | 383.1327 |
| 23 | 2,6-Difluorobenzyl bromide | 2,6-difluorobenzyl | 383.1338 |
| 24 | 3,4-Difluorobenzyl bromide | 3,4-difluorobenzyl | 383.1353 |
| 25 | Ethyl 1-bromocyclobutanecarboxylate | ethyl 1-cyclobutanecarboxylate | 383.1718 |

-continued

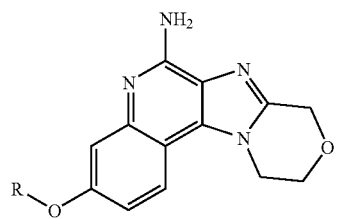

| Example | Reagent | R | Measured Mass (M + H) |
|---|---|---|---|
| 26 | 2-Bromo-4'-methylacetophenone | 4-methylphenyl-C(O)-CH₂- | 389.1642 |
| 27 | 4-Nitrobenzyl bromide | 4-nitrobenzyl | 392.1363 |
| 28 | 2-Bromo-4'-fluoroacetophenone | 4-fluorophenyl-C(O)-CH₂- | 393.1378 |
| 29 | 2-Bromo-3'-methoxyacetophenone | 3-methoxyphenyl-C(O)-CH₂- | 405.1522 |
| 30 | 2-Bromo-4'-methoxyacetophenone | 4-methoxyphenyl-C(O)-CH₂- | 405.1579 |
| 31 | Methyl 3-(bromomethyl)benzoate | 3-(methoxycarbonyl)benzyl | 405.1524 |
| 32 | Methyl 4-(bromomethyl)benzoate | 4-(methoxycarbonyl)benzyl | 405.1574 |
| 33 | 4-Phenoxybutyl bromide | PhO-(CH₂)₄- | 405.1904 |
| 34 | Benzyl 3-bromopropyl ether | PhCH₂O-(CH₂)₃- | 405.1953 |

-continued

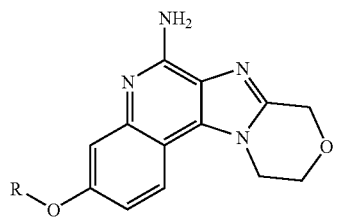

| Example | Reagent | R | Measured Mass (M + H) |
| --- | --- | --- | --- |
| 35 | Bromomethyl phenyl sulfone | phenyl-SO₂-CH₂- | 411.1104 |
| 36 | 2-(Trifluoromethyl)benzyl bromide | 2-CF₃-C₆H₄-CH₂- | 415.1384 |
| 37 | 3-(Trifluoromethyl)benzyl bromide | 3-CF₃-C₆H₄-CH₂- | 415.1410 |
| 38 | 4-(Trifluoromethyl)benzyl bromide | 4-CF₃-C₆H₄-CH₂- | 415.1411 |
| 39 | 3,4-Dichlorobenzyl bromide | 3,4-Cl₂-C₆H₃-CH₂- | 415.0749 |
| 40 | Bromodiphenylmethane | (C₆H₅)₂CH- | 423.1849 |
| 41 | 2-(Bromomethyl)pyridine, hydrobromide | 2-pyridyl-CH₂- | 348.1429 |
| 42 | 3-(Trifluoromethoxy)benzyl bromide | 3-CF₃O-C₆H₄-CH₂- | 431.1335 |

-continued

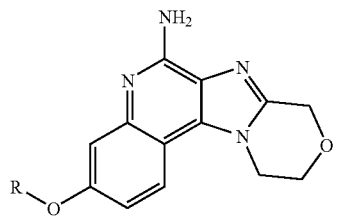

| Example | Reagent | R | Measured Mass (M + H) |
|---|---|---|---|
| 43 | 4-(Trifluoromethoxy)benzyl bromide | (4-trifluoromethoxybenzyl group) | 431.1347 |

Examples 44-51

Part A

DMF (25 mL) and potassium carbonate (2.7 g, 20 mmol) were added sequentially to a flask containing 6-amino-10,11-dihydro-8H-[1,4]oxazino[4',3':1,2]imidazo[4,5-c]quinolin-3-ol (1 g, 4 mmol). 1-Chloro-3-iodopropane (0.88 g, 4.3 mmol) was added and the reaction mixture was stirred at ambient temperature over night. Analysis by liquid chromatography/mass spectroscopy indicated mostly starting material. The reaction mixture was then heated at 60° C. over the weekend. The reaction mixture was transferred to a separatory funnel, diluted with ethyl acetate (about 300 mL), washed with water, and then filtered to remove a fine suspension. The organic layer was washed with water and then concentrated under reduced pressure to provide 3-(3-chloroethoxy)-10,11-dihydro-8H-[1,4]oxazino[4',3':1,2]imidazo[4,5-c]quinolin-6-amine as a yellow solid.

Part B

A secondary amine from the table below (1.1 equivalents) and anhydrous potassium carbonate (55 mg) were added to a test tube. A solution of 3-(3-chloroethoxy)-10,11-dihydro-8H-[1,4]oxazino[4',3':1,2]imidazo[4,5-c]quinolin-6-amine (33 mg, 0.1 mmol) in N,N-dimethylacetamide (1 mL) was added. The test tube was heated at 80° C. overnight (approximately 18 hours). The reaction mixture was filtered and the solvent was removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the secondary amine used for each example, the structure of the resulting compound, and the observed accurate mass for the isolated trifluoroacetate salt.

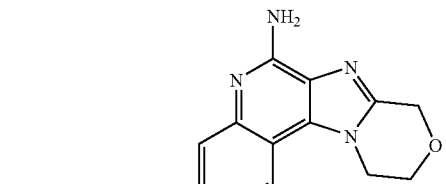

| Example | Reagent | R | Measured Mass (M + H) |
|---|---|---|---|
| 44 | Pyrrolidine | pyrrolidinyl | 368.2050 |
| 45 | Morpholine | morpholinyl | 384.1997 |
| 46 | 4-Methylpiperidine | 4-methylpiperidinyl | 396.2379 |
| 47 | 1-Methylpiperazine | 4-methylpiperazinyl | 397.2315 |
| 48 | N-Propylcyclopropanemethylamine | N-cyclopropylmethyl-N-propylamino | 410.2520 |
| 49 | N-Methylcyclohexylamine | N-cyclohexyl-N-methylamino | 410.2517 |

-continued

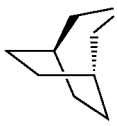

| Example | Reagent | R | Measured Mass (M + H) |
|---|---|---|---|
| 50 | 3-Azabicycl[3.2.2]nonane | (structure) | 422.2517 |
| 51 | Isonipecotamide | (structure) | 425.2265 |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 hours to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30° C. to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/nL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (1 molar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells (High Throughput Screen)

The CYTOKINE INDUCTION 1N HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and resuspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30 µM-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30° C. to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α a capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above-mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of Formula II:

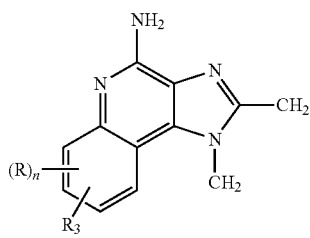

II wherein:
$R_3$ is —O—$R_{3-1}$ or $R_{3-2}$;
$R_{3-1}$ is selected from the group consisting of:
—Z—Y—$R_4$,
—Z—Y—X—Y—$R_4$,
—Z—$R_5$,
—Z-Het,
—Z-HetAr,
—Z-Het'-$R_4$,
—Z-HetAr'-$R_4$,
—Z-Het'-Y—$R_4$, and
—Z-HetAr'-Y—$R_4$;
$R_{3-2}$ is selected from the group consisting of:
—Z—Y—$R_4$,
—Z—Y—X—Y—$R_4$,
—Z—$R_5$,
—Z-Het,
—Z-Het'-$R_4$, and
—Z-Het'-Y—$R_4$;
R is selected from the group consisting of alkyl, alkoxy, hydroxy, halogen, and trifluoromethyl;
n is 0 or 1;
D is selected from the group consisting of —$(CH_2)_{1-4}$— and —$(CH_2)_c$—O—$(CH_2)_d$—; wherein c and d are integers and c+d is 0 to 3;
Z is selected from the group consisting of a bond, alkylene, alkenylene, and alkynylene, wherein alkylene, alkenylene, and alkynylene can be optionally interrupted with one or more —O— groups;
Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—C(=N—O—$R_8$)—,
—CH(—N(—O—$R_8$)-Q-$R_4$)—,

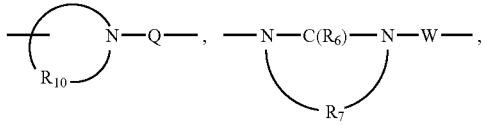

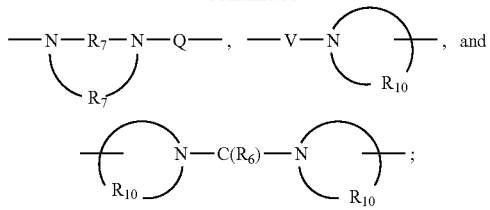

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

HetAr is heteroaryl which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

HetAr' is heteroarylene which can be unsubstituted or can be substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

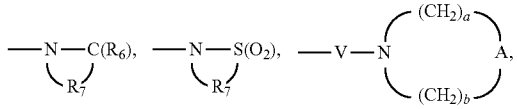

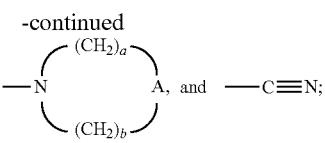

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, heteroarylalkylenyl, and arylalkylenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that Z is other than a bond when:
R$_3$ is —O—R$_{3-1}$, R$_{3-1}$ is —Z—Y—R$_4$ or —Z—Y—X—Y—R$_4$, and the Y group bonded to Z is —O—, —S—, —S(O)—, —O—C(R$_6$)—, —OC(O)—O—, —N(R$_8$)-Q-, —O—C(R$_6$)—N(R$_8$)—,

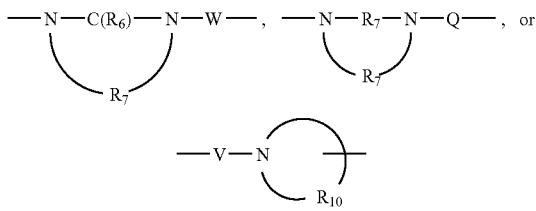

wherein V is
—O—C(R$_6$)— or —N(R$_8$)—C(R$_6$)—; or
R$_3$ is —O—R$_{3-1}$, R$_{3-1}$ is —Z—R$_5$, and R$_5$ is —C≡N,

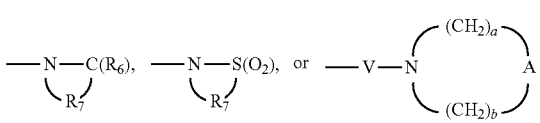

wherein V is
—O—C(R$_6$)— or —N(R$_8$)—C(R$_6$)—; or
R$_3$ is —O—R$_{3-1}$, R$_{3-1}$ is —Z-Het, —Z-Het'-R$_4$, or —Z-Het'-Y—R$_4$, and Z is attached to a nitrogen atom in Het or Het; or
R$_3$ is R$_{3-2}$, R$_{3-2}$ is —Z—Y—R$_4$, and —Y—R$_4$ is alkoxy;
or a pharmaceutically acceptable salt thereof.

2. The compound or salt of claim 1 wherein n is 0.
3. The compound or salt of claim 1 wherein R$_3$ is —O—Z—Y—R$_4$, —O—Z—Y—X—Y—R$_4$, —Z—Y—R$_4$, or —Z—Y—X—Y—R$_4$.

4. The compound or salt of claim 1 wherein:
Y is selected from the group consisting of —C(R$_6$)—, —C(R$_6$)—N(R$_8$)—, —N(R$_8$)-Q-, and

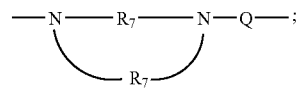

wherein Q is selected from the group consisting of a bond, —C(O)—, —C(O)—O—, —S(O)$_2$—, -and C(R$_6$)—N(R$_8$)—; R$_6$ is selected from the group consisting of =O and =S; R$_8$ is selected from the group consisting of hydrogen, $C_{1-4}$ alkyl, and $C_{1-4}$ alkoxy$C_{1-4}$ alkylenyl; and each R$_7$ is independently selected from $C_{2-3}$ alkylene; and
R$_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.

5. The compound or salt of claim 4 wherein Y is —C(O)— and R$_4$ is heterocyclyl.

6. The compound or salt of claim 1 wherein Z is alkylene, Y is —O—, —C(O)—NH—, —C(O)—O—, —C(O)—, —S(O)$_2$—, or —N(R$_8$)-Q-, and R$_4$ is hydrogen, alkyl, aryl, or arylalkylenyl wherein aryl and arylalkylenyl are unsubstituted or substituted by one or more substituents independently selected from the group consisting of alkyl, alkoxy, and halogen.

7. The compound or salt claim 1 wherein R$_3$ is —O—Z—R$_5$ or —Z—R$_5$.

8. The compound or salt of claim 1 wherein R$_3$ is —O—Z-Het, —O—Z-Het'-R$_4$, —Z-Het, or —Z-Het'-R$_4$.

9. The compound or salt of claim 1 wherein D is —CH$_2$—O—, and the ring containing D is

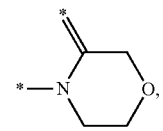

the bonds with * being part of the imidazo ring.

10. A pharmaceutical composition comprising a therapeutically effective amount of a compound or salt of claim 1 and a pharmaceutically acceptable carrier.

11. A method of inducing cytokine biosynthesis in an animal comprising administering an effective amount of a compound or salt of claim 1 to the animal.

12. A method of treating a viral disease in an animal in need thereof comprising administering a therapeutically effective amount of a compound or salt of claim 1 to the animal.

13. A method of treating a neoplastic disease in an animal in need thereof comprising administering a therapeutically effective amount of a compound or salt of claim 1 to the animal.

14. The compound of claim 1, wherein Formula II is Formula X:
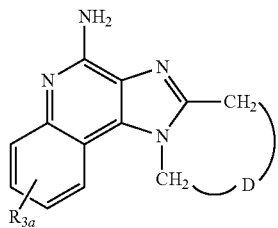
wherein:
$R_{3a}$ is benzyloxy;
$R_{3a}$ is at the 7- or 8-position; and
D is selected from the group consisting of —$(CH_2)_{1-4}$— and —$(CH_2)_c$—O—$(CH_2)_d$—; wherein c and d are integers and c+d is 0 to 3;
or a pharmaceutically acceptable salt thereof.
* * * * *

UNITED STATES PATENT AND TRADEMARK OFFICE
CERTIFICATE OF CORRECTION

PATENT NO. : 8,093,390 B2
APPLICATION NO. : 11/884186
DATED : January 10, 2012
INVENTOR(S) : Michael J Rice It is certified that error appears in the above-identified patent and that said Letters Patent is hereby corrected as shown below:

In the Specification:

Column 1
Lines 14-20, below "Feb. 11, 2005." delete "CROSS REFERENCE TO RELATED APPLICATIONS The present invention claims priority to U.S. Provisional Application Ser. No. 60/652,281, filed Feb. 11, 2005, which is incorporated herein by reference.".

Column 4
Line 56, delete "Z—Y" and insert -- —Z—Y --, therefor.

Column 5
Line 15, delete "$R_9$)—," and insert -- $R_8$)—, --, therefor.

Column 6

Lines 18-19, delete " 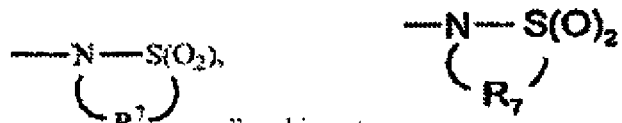 " and insert -- 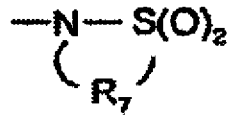 --, therefor.
Line 26, delete "R" and insert -- $R_6$ --, therefor.
Line 42, delete "—N($R_6$)" and insert -- —N($R_8$) --, therefor.

Column 7

Lines 1-5, delete " 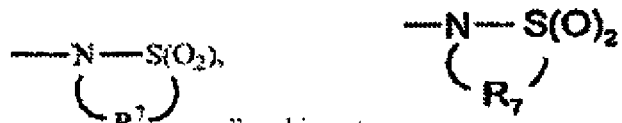 " and insert -- 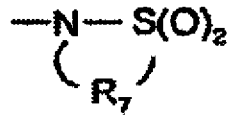 --, therefor.
Line 67, delete "—O—C)—," and insert -- —O—C($R_6$)—, --, therefor.

Signed and Sealed this
Twenty-eighth Day of October, 2014

Michelle K. Lee
*Deputy Director of the United States Patent and Trademark Office*

Column 9

Lines 7-10, delete "  " and insert --  --, therefor.
Line 32, delete "—N(R₉)—" and insert -- —N(R₈)— --, therefor.
Line 54, delete "—N(R₉)—" and insert -- —N(R₈)— --, therefor.

Lines 58-60, delete " 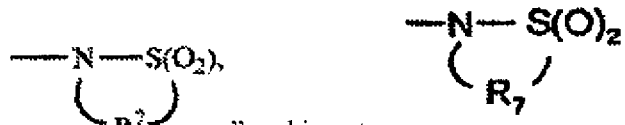 " and insert -- 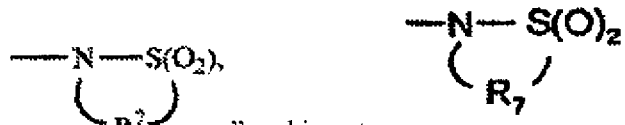 --, therefor.
Line 64, delete "—C(R₅)—;" and insert -- —C(R₆)—; --, therefor.

Column 11
Line 17, delete "N(R₈)-Q-," and insert -- —N(R₈)-Q-, --, therefor.
Line 22, delete "—C(=O—N—O—R₉)—," and insert -- —C(=N—O—R₈)—, --, therefor.

Column 12

Lines 25-26, delete "  " and insert --  --, therefor.

Column 13

Lines 12-15, delete " 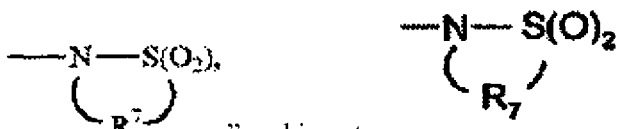 " and insert -- 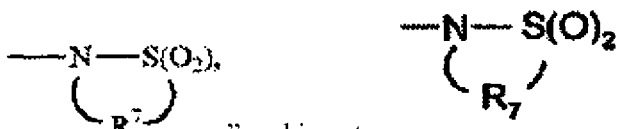 --, therefor.
Line 44, delete "—C(—NY₁)—" and insert -- —C(=NY₁)— --, therefor.

Column 16
Line 45, delete "bicylic" and insert -- bicyclic --, therefor.

Column 18
Lines 61-62, delete "substitutents" and insert -- substituents --, therefor.

Column 19
Line 20, delete "R" and insert -- R₄ --, therefor.
Line 21, delete "R" and insert -- R₄ --, therefor.
Line 38, delete "R₉" and insert -- R₈ --, therefor.

Column 20
Line 18, delete "substitutents." and insert -- substituents. --, therefor.

Column 22
Line 9, delete "$R_5$" and insert -- $R_8$ --, therefor.

Column 23
Line 42, delete "α-Amino-$C_{2-11}$" and insert -- α-amino-$C_{2-11}$ --, therefor.
Line 59, delete "—C($R_8$)—," and insert -- —C($R_6$)—, --, therefor.

Column 24
Line 11, delete "—N($R_9$)—" and insert -- —N($R_8$)— --, therefor.
Line 17, after "—S(O)$_2$—" insert -- . --.

Column 25
Line 5, delete "alkoxy$C_4$" and insert -- alkoxy$C_{1-4}$ --, therefor.

Column 27
Line 59, delete "Katritsky," and insert -- Katritzky, --, therefor.

Column 28
Line 22, delete "chromatography," and insert -- chromatography), --, therefor.

Column 32
Line 3, delete "—$F_4$," and insert -- —$R_4$, --, therefor.
Line 4, delete "R," and insert -- $R_4$, --, therefor.

Column 33
Line 42, delete "$C_1$—$R_7$S(O)$_2$Cl" and insert -- Cl—$R_7$S(O)$_2$Cl --, therefor.
Line 48, delete "insoluble" and insert -- isolable --, therefor.
Line 56, delete "X=X" and insert -- XXIX --, therefor.

Column 34
Line 39, delete "($R_B$)H" and insert -- ($R_8$)H --, therefor.
Line 46, delete "HN($R_9$)$R_4$" and insert -- HN($R_8$)$R_4$ --, therefor.
Line 47, delete "($R_4$)$R_9$N—" and insert -- $R_4$($R_8$)N— --, therefor.
Line 55, delete "N($R_9$)H," and insert -- N($R_8$)H, --, therefor.

Column 35
Line 9, after "Boc" insert -- , --.

Column 40
Line 28, delete "XIV," and insert -- XXXIV, --, therefor.
Line 63, delete "XIII" and insert -- XXXIII --, therefor.

Column 41
Line 7, delete "XXIII" and insert -- XXXIII --, therefor.

CERTIFICATE OF CORRECTION (continued)

Column 42
Line 4, delete "1V," and insert -- IV, --, therefor.
Line 39, delete "XXVIII" and insert -- XXXVIII --, therefor.
Line 62, delete "X" and insert -- XXXIX --, therefor.

Column 43
Line 62, delete "a. quinoline" and insert -- a quinoline --, therefor.

Column 46
Line 57, delete "—C(—NY$_1$)—R'," and insert -- —C(=NY$_1$)—R', --, therefor.

Column 48
Line 55, delete "cytolidnes." and insert -- cytokines. --, therefor.

Column 49
Line 39, delete "carnii" and insert -- carinii --, therefor.
Line 54, delete "Ommen's" and insert -- Omenn's --, therefor.

Columns 55-56
Line 1 (Example 3), delete "4-(Chloromethy)lthiazole" and insert -- 4-(Chloromethyl)thiazole --, therefor.

Column 68
Line 34, delete "pg/nL" and insert -- pg/mL --, therefor.
Line 54, delete "(1 molar)" and insert -- (μmolar) --, therefor.
Line 65, delete "1N" and insert -- 1N --, therefor.

In the Claims:

Column 71

Lines 8-16, in claim 1, delete " 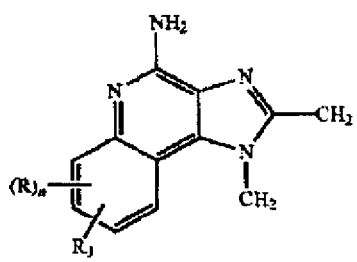 " and insert -- 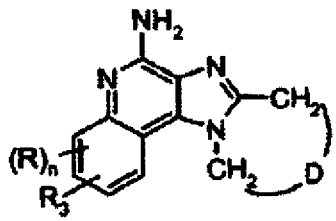 --, therefor.

Column 71
Line 48, in claim 1, above "—S(O)$_{0-2}$—," insert -- —O—, --.

Column 72

Lines 64-65, in claim 1, delete "  " and insert -- , --, therefor.

Column 73

Lines 51-54, in claim 1, delete " 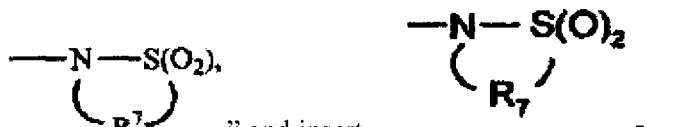 " and insert -- , --, therefor.

Line 60, claim 1, delete "Het;" and insert -- Het'; --, therefor.

Column 74
Line 3, in claim 4, delete "—C(R$_6$)—N(R$_8$)—," and insert
-- —C(R$_6$)—,—C(R$_6$)—N(R$_8$)—, --, therefor.
Line 12, in claim 4, delete "-and" and insert -- and --, therefor.
Line 38, in claim 7, delete "salt claim 1" and insert -- salt of claim 1 --, therefor.